US008501169B2

(12) United States Patent
Sanz Herranz et al.

(10) Patent No.: US 8,501,169 B2
(45) Date of Patent: Aug. 6, 2013

(54) MICROORGANISMS FOR IMPROVING THE HEALTH OF INDIVIDUALS WITH DISORDERS RELATED TO GLUTEN INGESTION

(75) Inventors: Yolanda Sanz Herranz, Bujassot (ES); Esther Sanchez Sanchez, Bujassot (ES); Marcela Susana Medina, Bujassot (ES); Giada De Palma, Bujassot (ES); Inmaculada Nadal Gimenez, Bujassot (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 19 days.

(21) Appl. No.: 12/810,369

(22) PCT Filed: Dec. 23, 2008

(86) PCT No.: PCT/ES2008/070243
§ 371 (c)(1),
(2), (4) Date: Jul. 21, 2010

(87) PCT Pub. No.: WO2009/080862
PCT Pub. Date: Jul. 2, 2009

(65) Prior Publication Data
US 2010/0310520 A1    Dec. 9, 2010

(30) Foreign Application Priority Data
Dec. 24, 2007   (ES) .................................. 200703427

(51) Int. Cl.
*C12N 1/20*   (2006.01)
(52) U.S. Cl.
USPC ...................................... 424/93.4; 435/252.1
(58) Field of Classification Search
None
See application file for complete search history.

(56) References Cited

U.S. PATENT DOCUMENTS

| | | | |
|---|---|---|---|
| 2003/0215467 A1* | 11/2003 | Collins et al. | 424/234.1 |
| 2005/0249719 A1 | 11/2005 | Shan | |
| 2006/0251633 A1* | 11/2006 | Salvadori et al. | 424/93.45 |
| 2006/0286601 A1 | 12/2006 | Marti | |
| 2007/0142622 A1 | 6/2007 | Peakman | |
| 2007/0160609 A1 | 7/2007 | Maroun | |
| 2007/0161572 A1 | 7/2007 | Sollid | |
| 2007/0184049 A1 | 8/2007 | Fox | |
| 2007/0196501 A1 | 8/2007 | Paterson | |

FOREIGN PATENT DOCUMENTS

| | | |
|---|---|---|
| WO | WO 03/010297 | 2/2003 |
| WO | WO 2004076615 | 9/2004 |
| WO | WO 2005032567 | 4/2005 |
| WO | WO 2007025247 | 3/2007 |
| WO | WO 2007108763 | 9/2007 |

OTHER PUBLICATIONS

Medina, et al., "Bifidobacterium strains suppress in vitro the pro-inflammatory milieu triggered by the large intestinal microbiota of coeliac patients," Journal of Inflammation, vol. 5, No. 19 (doi:10.1186/1476-9255-5-19; pp. 1-13; published online Nov. 3, 2008).*
International Search Report of International PCT application No. PCT/ES2008/070243 mailed Apr. 16, 2009.
Altschul et al, J. Mol Biol., 1990, 215, 403-410.
Collado, et al., J Clin Pathol., 2009, 62, 264-269.
De Angelis, et al, Biochimica Biophysica Acta, 2006, 1762(1):80-93.
De Stefano et al., European Journal of Pharmacology, 2007, 566 (1-3):192-199.
Di Cagno, et al., Applied Environmental Microbiology, 2004, 70(2):1088-1096.
Favier, et al. Applied Environmental Microbiololgy, 2002, 68(1), 219-226.
Forsberg, et al., International Immunology, 2007 19:8, 993-1001.
Gass, et al., Gastroenterology, 2007, 133:472-480.
Green, et al., Annual Review Med., 2006, 57:207-221.
Gross, et al., Inflamm Bowel Dis., 2007, 13(7):918-932.
Hermsdorf, Analytical Biochemistry, 1978, 90:835-839.
Jabri, et al., Gastroenterology, 2000, 118 :867-879.
Jelínková, et al., FEBS Lett., 2004, 571(1-3):81-85.
Jonhson, "Similarity analysis of rRNAs", In Methods for General and Molecular Bacteriology, Gerhardt, P.; et al., Eds., American Society for Microbiology, Washington, DC, 1994, 683-700.
Kaufman, et al., Applied and Environmental Microbiology, 1997, 63:4, 1268-1273.
Lammers, et al., FEMS Immunology and Medical Microbiology, 2003, 38: 165-172.
Mention, et al., Gastroenterology, 2003, 125, 730-745.
Nadal, et al., Journal of Medical Microbiololgy, 2007; 56:1669-1674.
Rizzello, et al., Applied and Environmental Microbiology, 2007, 73:14, 4499-4507.
Salvati, et al., Gut, 2005, 54, 46-53.
Sanz, et al., FEMS Immunol Med Microbiol., 2007, 51(3):562-568.
Satokari, et al., Applied and Environmental Microbiology, 2001, 67:2, 504-513.
Silano, et al., Pediatric Research, 2007, 61:1, 67-71.
Stepniak, et al.,Trends in Biotechnology, 2006, 24:10, 433-434.
Ventura, et al., Applied and Environmental Microbiology, 2003, 69(11):6908-6922.

\* cited by examiner

*Primary Examiner* — Cherie M Stanfield
*Assistant Examiner* — Paul D. Pyla
(74) *Attorney, Agent, or Firm* — Merchant & Gould P.C.

(57) ABSTRACT

The invention relates to microorganisms for the treatment of food allergies, specifically coeliac disease, as well as to methods for the selection thereof. The action mechanisms of said microorganisms include: (i) the regulation of the innate and adaptive immunological responses; (ii) the reduction of the concentration of toxic gluten peptide epitopes in the intestinal lumen; (iii) the strengthening of the barrier defence function against harmful antigens and bacteria; and (iv) the provision of enzymatic activities that promote digestion.

17 Claims, 2 Drawing Sheets

MICROORGANISMS FOR IMPROVING THE HEALTH OF INDIVIDUALS WITH DISORDERS RELATED TO GLUTEN INGESTION

This application is a National Stage Application of PCT/ES2008/070243, filed 23 Dec. 2008, which claims benefit of Serial No. P200703427, filed 24 Dec. 2007 in Spain and which applications are incorporated herein by reference. To the extent appropriate, a claim of priority is made to each of the above disclosed applications.

SECTOR OF THE TECHNIQUE

The invention relates to the Food Industry and Pharmaceutics sector. Specifically, the invention relates to the field of probiotics and derived products in the form of functional foods and new foods, probiotics, synbiotics, nutraceuticals or food supplements and pharmaceutical compositions with clinical applications.

STATE OF THE TECHNIQUE

Coeliac disease is an enteropathy, affection of the intestine, of an immune nature caused by permanent intolerance to the gluten proteins from cereals, suffered by genetically predisposed individuals. The disease has a broad clinical spectrum and includes typical, atypical, silent and potential forms. The typical forms most frequently present in the first years of life (6-24 months) and manifest mainly with intestinal symptoms and related alterations (malabsorption, chronic diarrhea, weight loss, abdominal fullness, delayed growth, etc.). It is currently the most common chronic disease, with a prevalence of 0.7 to 2.0% among the general population and 15 to 20% among first-degree relatives. Also, gluten ingestion and coeliac disease are associated with other disorders such as Down's syndrome, diabetes Mellitus type 1, dermatitis herpetiformis, myopathy, multiple sclerosis, arthritis, autism, schizophrenia, depression, lymphomas, and ataxia. The relationship between gluten ingestion and psychiatric, neurological and behavioural disorders is considered a result of the generation of bioactive peptides, such as exorphins, having opioid activity.

Gluten proteins (gliadins and analogous prolamins and glutenins) represent the main environmental factor that triggers coeliac disease and other related disorders. These proteins contain peptide sequences rich in proline and glutamine, making them more resistant to digestive enzymes than other proteins in the diet and, therefore, capable of remaining in the intestinal lumen. In genetically predisposed individuals, these peptides are responsible for an anomalous reaction that involves both the innate and the adaptive immune system and that, globally, lead to chronic inflammation of the intestinal mucosa, increased intraepithelial lymphocytes, crypt hyperplasia, and a progressive deterioration of intestinal villi including their total disappearance. The toxic peptides generated following the ingestion of gluten may pass across the intestinal epithelium and are recognised by the HLA-DQ2 or HLA-DQ8 molecules of antigen-presenting cells, preferably following their deamidation through the action of tissular transglutaminase. Thus, they are presented to T-cell receptors, producing their activation. This involves the expression of the CD4 antigen, also known as helper (Th), and its differentiation into lymphocyte subpopulations, thus involving acquired immunity. The Th2 subpopulation interacts with B cells which differentiate themselves into plasma cells and produce the antibodies anti-gliadin, anti-endomysium, and anti-tissular transglutaminase. Subpopulation Th1 is responsible for an increase in the secretion of pro-inflammatory cytokines (mainly IFN-γ) and in the IFN-γ/IL-10 ratio (Salvati et al. 2005. Recombinant human interleukin 10 suppresses gliadin dependent T cell activation in ex vivo cultured coeliac intestinal mucosa. Gut. 54: 46-53). Gluten peptides can also trigger a response in the intestinal epithelium mediated by the cytokine IL-15, involving the innate immune system (Green and Jabri 2006. Celiac disease. Ann Rev Med. 57:207-21). Ingested gliadins stimulate the production of IL-15 in epithelial cells, which favours the clonal expansion of intraepithelial cytotoxic CD8 T lymphocytes and the expression of IFN-γ (Jabri et al. 2000. Selective expansion of intraepithelial lymphocytes expressing the HLA-E-specific natural killer receptor CD94 in celiac disease. Gastroenterology. 118:867-79; Mention et al., 2003. Interleukin 15: a key to disrupted intraepithelial lymphocyte homeostasis and lymphomagenesis in celiac disease. Gastroenterology. 125: 730-45; Forsberg et al. 2007. Concomitant increase of IL-10 and pro-inflammatory cytokines in intraepithelial lymphocyte subsets in celiac disease. Int Immunol. 2007:19, 993-1001). The composition of the intestinal microbiota of coeliac disease patients also presents an imbalance in relation to that of healthy control individuals, characterised by the predominance of pro-inflammatory bacteria and a reduced proportion and composition of lactic acid bacteria and bifidobacteria. (Sanz et al., 2007. Differences in faecal bacterial communities in coeliac and healthy children as detected by PCR and denaturing gradient gel electrophoresis. FEMS Immunol Med. Microbiol. 51(3):562-8. Nadal et al., 2007. Imbalance in the composition of the duodenal microbiota of children with coeliac disease. J Med Microbiol. 2007 December; 56(Pt 12):1669-74; Collado et al. 2009. Specific duodenal and faecal bacterial groups are associated with paediatric celiac disease. J Clin Pathol. 62: 264-269). In the intestinal lumen and epithelium, the combination of gluten with an increase in harmful bacteria can act as a trigger factor or favour the pathological process and pro-inflammatory reactions in cases of active coeliac disease, as well as in other related disorders. Likewise, the presence or absence of certain bacterial species can favour or protect against gluten toxicity.

Coeliac disease has a high incidence and severity; however, currently there is no therapy for these patients. The only alternative is to maintain a strict lifelong gluten-free diet. The compliance with this dietary recommendation is difficult and patients continue suffering gastrointestinal symptoms, nutritional deficiencies, and higher health risks (immune disorders, osteoporosis, infertility, cancer, etc.) and the balance of their intestinal ecosystem is never fully restored. Additionally, individuals with refractory coeliac disease (5-10%) do not respond to this dietary recommendation.

Therapeutic options or co-adjuvants that are currently under research for treating coeliac disease include oral administration of proteolytic enzymes obtained from plants or microorganisms to accelerate gastrointestinal digestion of gluten peptides (Shan et al. 2005. Enzyme treatment of foodstuffs for celiac sprue. 20050249719/A1; Marti et al. 2006. Prolyl endopeptidase mediated destruction of T cell epitopes in whole gluten. 20060286601/A1; Stepniak y Koning. 2006. Enzymatic gluten detoxification: the proof of the pudding is in the eating! Trends Biotechnol. 24:433-4; Gass et al. 2007. Combination enzyme therapy for gastric digestion of dietary gluten in patients with celiac sprue. Gastroenterology. 133: 472-80). The effectiveness of this strategy has been demonstrated in model systems using protein and peptide preparations or their recombinant equivalents, but studies that demonstrate its effectiveness in vivo are still required in individuals who ingest gluten as it is in foods. Despite the potential benefits of this therapy as an adjuvant in a gluten-free diet, its effects will be highly dependent on the time of ingesting the enzyme preparation and will only allow the occasional ingestion of gluten reducing the toxicity threshold. Other proposed alternatives include the development of tissular transglutaminase inhibitor compounds (Khosla et al., 2006. Transglutaminase inhibitors and methods of use thereof WO2007025247), antibodies capable of capturing the gliadin peptides (Fox, 2007. Antibody therapy for treatment of diseases associated with gluten intolerance. 20070184049/A1), compounds that block the binding sites of gluten peptides to HLA-DQ2 or HLA-DQ8 molecules (Sollid et al. 2007. Drug therapy for celiac sprue. 20070161572/A1); Peakman and Chicz. 2007. Peptide epitopes recognized by disease promoting CD4+ T lymphocytes. 20070142622/A1), pro-inflammatory cytokine antagonists such as IFN-γ (Maroun et al., 2007. Interferon antagonists useful for the treatment of interferon related diseases. 20070160609/A1), the oral administration of recombinant regulatory cytokines (Salvati et al., 2005. Recombinant human interleukin 10 suppresses gliadin dependent T cell activation in ex vivo cultured coeliac intestinal mucosa. Gut. 2005; 54:46-53), inhibitors of adhesion molecules involved in the inflammatory reactions, and antagonists of zonulin responsible for increases in paracellular permeability (Paterson and Ginski. 2007. Formulations for a tight junction effector US20070196501/A1). These strategies entail the modification of molecules involved in several biological processes and their use could lead to undesired secondary effects. In the food industry strategies are being developed to avoid the presence of toxic epitopes in the food we ingest through the genetic manipulation of certain varieties of wheat and the use of proteolytic enzymes and lactobacilli during the cereal fermentation processes, which can degrade the toxic epitopes. In this way, the objective is to introduce improvements in the diet of coeliac patients and to provide them with a wider variety of products but without preventing or treating the disease itself (Rizzello et al. 2007. Highly efficient gluten degradation by lactobacilli and fungal proteases during food processing: new perspectives for celiac disease. Appl Environ Microbiol. 73:4499-507).

The use of strains belonging to the *Bifidobacterium* genus as probiotics or pharmaceutical preparations for the treatment and prevention of coeliac disease and related disorders and is the basis of the present invention. The benefits of bifidobacteria specifically selected for this purpose are numerous. Bifidobacteria have a special capability to colonise the intestinal tract of newborns, significantly contributing to the development of their defences (immune and others) and to the oral tolerance to dietary antigens. This group of bacteria is one of the major constituents of intestinal microbiota in the first years of life, particularly in breast-fed children.

DESCRIPTION OF THE INVENTION

Brief Description of the Invention

The invention provides a method for selecting microorganisms or microbial strains capable of modulating the immune response. These microorganisms, preferably belonging to the *Bifidobacterium* genus, are capable of being used for treatment or prevention of immune-mediated diseases such as coeliac disease, due to its immunomodulatory capacities.

Also, the invention provides a new strain of the *Bifidobacterium* genus (CECT 7347; hereinafter "strain of the invention" (IATA-ES1), its cellular components, secreted molecules and compounds resulting from its metabolism and any combinations thereof with each other and/or with other microorganisms or bioactive compounds, in the form of preparations designed to reduce the risks and improve the health and quality of life of individuals with coeliac disease and other disorders related to gluten ingestion (allergy, autism, ataxia, diabetes, multiple sclerosis, etc.).

The strain of the invention was isolated from the faeces of healthy breast-fed infants and identified by sequencing of the 16 S rRNA and tuf genes. This strain has immunomodulatory properties capable of regulating the Th1-type pro-inflammatory responses characteristic of coeliac disease and related diseases (multiple sclerosis, diabetes, ataxia, etc.), as well as the Th2-type immune responses characteristic of IgE-mediated dietary protein allergies, which result from the ingestion of wheat and other cereal proteins. The strain of the invention is characterised by inducing low production of the Th1 cytokine IFN-γ and of the pro-inflammatory cytokine IL-1, and by inducing high production of the regulatory cytokines IL10 and TGF-β in peripheral blood mononuclear cells (PBMCs). The profile of cytokines induced by this strain is not a common characteristic of all bifidobacteria and human intestinal lactic acid bacteria and makes it particularly suited to modulate the anomalous immune response brought about by gluten proteins in predisposed individuals. Its combination with other microorganisms, such as for example *B. longum* ATCC15707, can potentiate the synthesis of the regulatory cytokine IL-10 beneficial for controlling the inflammation process characteristic of these pathologies. The unviable bacteria (inactivated through various procedures, such as heat, freezing-thawing, radiation, etc.) maintain their immunomodulatory properties.

The strain of the invention is capable of taking up and hydrolysing the gluten peptides responsible for these disorders, reducing the concentration of toxic epitopes and their pathogenic potential. The strain of the invention possesses specific peptidases for hydrolysing substrates containing proline, which are common in gluten proteins. The combinations of this with other strains of bifidobacteria that possess peptidases of diverse specificity allow their action to be complemented, favouring the degradation of toxic epitopes. The combination of bifidobacteria with other microorganisms such as *Lactococcus lactis* NCDO712, which has a cell-wall anchored proteinase, also potentiates the hydrolytic effects due exclusively to the action of the bifidobacteria.

The strain of the invention is capable of modulating the immune response provoked by the gluten peptides by means of: (i) inducing the synthesis of regulatory cytokines (IL-10), (ii) reducing the production of pro-inflammatory cytokines IFN-γ, IL-1, IL-8 and IL-15 derived from the innate and adaptive immune response and (iii) inhibiting the pro-inflammatory pathway mediated by the nuclear factor κB (Example 3, Table 3).

The strain of the invention, as well as the derived compounds thereof is also capable of inhibiting pathogenic bacteria isolated from the intestinal microbiota of coeliac disease patients, with pro-inflammatory potential and virulence factors favouring the reestablishment of intestinal balance (Example 4, Tables 4 and 5). These strains are also capable of inhibiting the pro-inflammatory response of the intestinal bacteria of active coeliac disease patients and of those under a gluten-free diet, reducing the synthesis of pro-inflammatory cytokines (TNF-α and IFN-γ) and increasing that of regulatory cytokines (IL-10).

The strain of the invention also possesses metabolic activities (for example: phosphatase, esterase, lipase, galactosidase, glucosidase and N-acetyl-glucosaminidase) which favour the digestion of nutrients and improve the syndrome of malabsorption and malnutrition characteristic of coeliac patients.

The strain of the invention possesses the capacity to adhere to mucin (1-4%) and is stable under conditions of gastrointestinal stress (acid pH and high concentration of bile; Example 5, Table 6 and Table 7) and of the technological processes of food storage and preparation (refrigeration, lyophilisation, fermentation, etc.). In vivo it is capable of surviving transit in humans following oral administration. All of these properties guarantee its prolonged persistence and effectiveness in the intestine and its use as probiotics and synbiotics (combinations of pro and prebiotics). They also guarantee its use in the form of functional foods, novel foods, supplements, nutraceuticals and drugs for reducing the risks and improving the health and quality of life of subjects with coeliac disease as well as with other disorders related to gluten ingestion.

Thus, a first aspect of the invention relates to a method for selecting microorganisms or strains of microorganisms capable of modulating the immune response to food allergies, which comprises: (a) isolating microorganisms from samples, preferably faeces, from healthy individuals, preferably breast-fed infants, and (b) selecting those microorganisms of previous stage capable of modulating the immune response and hydrolysing, inactivating or interfering with the mechanism of action of at least one agent that causes food allergies, preferably coeliac disease. Preferably, the microorganisms selected in stage (a) belong to potentially probiotic genera or species. In a preferred embodiment, the immune response modulated by the microorganism obtained in stage (a) is the pro-inflammatory responses of type Th1 or Th2. Also, the microorganisms obtained in stage (a) and (b), alternatively or in addition to their modulating capacity of the immune response, may be selected for their capacity to increase the viability and/or integrity of epithelial cells improving the intestinal barrier function.

The microorganisms selected by the above method or capable of hydrolysing, inactivating or interfering with the mechanisms of action of at least one agent that causes food allergies and modulating the immune response can be used for the treatment or prevention of food allergies (hereinafter "microorganisms of the invention"). Thus, a second aspect of the invention relates to the use of these microorganisms as a medicament or food compositions, preferably, for the treatment or prevention of food allergies. These microorganisms may belong to any bacterial genus or species, preferably the genus *Bifidobacterium* and, more preferably, to the species *B. longum*.

A third aspect of the invention relates to a bacterial strain with deposit number CECT 7347.

A fourth aspect of the invention relates to a composition (hereinafter, the "composition of the invention") which comprises at least one of the microorganisms of the invention, preferably the strain of the invention, where moreover it is preferably present in such composition in a proportion between 0.1 and 99.9%, preferably between 1% and 99% and more preferably between 10% and 90%. This composition may additionally comprise other microorganisms or media that potentiate, among others, the immunomodulatory capacity of the microorganism or strain of the invention or its capacity to hydrolyse, inactivate or interfere with the mechanisms of action of the agents causing food allergies.

A fifth aspect of the invention relates to a composition that can be obtained from the bioactive compounds derived from the microorganisms of the invention like, as way of illustration and without limiting the scope of the invention, the supernatant of a culture of any of the microorganisms of the invention (hereinafter "supernatant of the invention"), the extracts obtained from the pure or mixed culture of any of the microorganisms of the invention or strain of the invention (hereinafter, "extract of the invention"), the cell components or sub-cell fractions, metabolites and products secreted by the microorganisms or strain of the invention obtained by means of physical-chemical and/or biotechnological techniques known to an expert in the art. These bioactive compounds derived from the microorganism of the invention, hereinafter "derived bioactive compounds of the invention", may be used for the preparation of foods, supplements, nutraceuticals, products based on probiotics or synbiotics, novel foods or medicaments, and likewise their different uses also form part of the invention.

Another aspect of the invention relates to a support material for the preparation of food products that comprises the composition of the invention or at least one microorganism of the invention, preferably, the strain of the invention. In a preferred embodiment, the microorganism of the invention is contained in the support material in a quantity of at least about $10^5$ cfu/g of support material, preferably between $10^6$ cfu/g and $10^{12}$ cfu/g, more preferably between $10^6$ cfu/g and $10^{10}$ cfu/g. According to the foregoing, any food product or supplement comprising the composition of the invention or support material of the invention also forms part of the invention.

Another aspect of the invention relates to a pharmaceutical composition or food composition that comprises any of the following compounds: the composition of the invention, the derived bioactive compounds of the invention, the supernatant of the invention, the extract of the invention, a microorganism of the invention, the strain of the invention and, optionally, pharmacologically acceptable media and/or excipients. The quantity of microorganisms that the pharmaceutical composition or food composition must contain will vary according to the type of pathology it is designed to treat. Preferably said pathology is a food allergy and, more preferably, coeliac disease. In the case of the preparation of food compositions, and in accordance with the present invention, at least one microorganism of the invention or derived bioactive compound of the invention, is incorporated into a support material preferably in an amount of between $10^5$ cfu/g and $10^{14}$ cfu/g of support material, more preferably between about $10^8$ cfu/g and $10^{13}$ cfu/g, and even more preferably between $10^7$ cfu/g and $10^{12}$ cfu/g, in the case of a microorganism of the invention, and in the case of a derived bioactive compound of the invention in a proportion of between 0.1 and 99.9%, preferably between 1% and 99% and more preferably between 10% and 90%. These food compositions can be used for the preparation of nutraceuticals, functional foods, probiotics, synbiotics, nutritional supplements or any other type of product designed for the treatment or prevention preferably of food allergies and, more preferably, of coeliac disease.

The pharmaceutical composition or food composition of the invention can be found preferably in the form of tablets, capsules, microcapsules, powders, solutions, pastes, etc.

Another aspect of the invention relates to the composition of the invention, derived bioactive compounds of the invention, the supernatant of the invention, extract of the invention, pharmaceutical composition of the invention, subcellular fractions of the invention, the food composition of the invention or the support material of the invention, wherein the microorganism of the invention or the strain of the invention is combined with another microorganism, a supernatant obtained from its culture or the subcellular fractions thereof. Preferably, said microorganism belongs to the genus *Lacto-*

*coccus*, preferably to the species *Lactococcus lactis* and, more preferably, is the strain *Lactococcus lactis* NCDO712.

A final aspect of the invention relates to the different forms of presentation of the composition of the invention which may be formulated as a food, nutraceutical, pharmaceutical preparation, supplement, probiotics or synbiotic, or novel foods.

Definitions:

Breast-fed infants: throughout the description this term will refer preferably to healthy individuals, preferably aged less than two years old, more preferably less than 1 year old and more preferably less than 6 months old, who have been predominantly breast-fed.

Healthy individual: this term refers preferably to someone who does not suffer any type of chronic or acute pathology according to the criteria of specialist doctors. Preferably said pathology provokes inflammation of the intestinal epithelium, more preferably coeliac disease.

Food allergies: throughout the description this term will refer preferably to those food allergies caused preferably by milk, eggs, pulses, nuts, crustaceans, fish, molluscs, sesame, sunflower seeds, cotton seeds, poppy seeds, beans, peas, lentils and, more preferably, by gluten.

Th1-type pro-inflammatory response: the response to a stimulus that causes a high production of Th1-type cytokines, and preferably of the cytokine IFN-γ that is preferably at least 100 times, more preferably at least 15 times, more preferably at least 10 times and even more preferably at least 4 times higher than the control.

Th2-type pro-inflammatory response: the response to a stimulus that causes a high production of Th2-type cytokines, and preferably of the cytokine IL4 that is at least 100 times, more preferably at least 15 times, more preferably at least 10 times and even more preferably at least 4 times higher than the control.

Potentially probiotic genera or species: Preferably throughout the description this term will refer to the species and strains of the following phylogenetic divisions and prokaryote genera: *Archaea, Firmicutes, Bacteroidetes, Proteobacteria, Actinobacteria, Verrucomicrobia, Fusobacteria, Spirochaetes, Fibrobacters, Deferribacteres, Deinococcus, Thermus, Cianobacteria, Methanobrevibacterium, Bifidobacterium, Lactobacillus, Streptococcus, Leuconostoc. Peptostreptococcus, Pediococcus, Lactococcus, Enterococcus, Ruminococcus, Coprococcus, Subdolingranulum, Dorea, Bulleidia, Anaerofustis, Gemella, Roseburia, Catenibacterium, Dialister, Anaerotruncus, Staphylococcus, Micrococcus, Propionibacterium, Enterobacteriaceae, Faecalibacterium, Bacteroides, Parabacteroides, Prevotella, Eubacterium, Akkermansia, Bacillus, Butyrivibrio, Clostridium*, etc. As well as the species and strains of fungi and yeasts *Saccharomyces, Candida, Pichia, Debaryomyces, Torulopsis, Aspergillus, Rhizopus, Mucor, Penicillium*, among others.

Media: this term will refer preferably to culture media, substrates, prebiotics, fibres, bioactive compounds, excipients, ingredients, etc. which improve any characteristic of the microorganisms of the invention for use, preferably, in the preparation of medicaments, nutritional compositions, compositions, support materials, supernatants and foods of the invention (for example, stability, immunomodulatory capacities, capacities of adhesion, fermentation, hydrolysation or inactivation of allergy-causing agents, etc.)

Support material: preferably, the support material is a food composition selected from milk, yoghurt, cheese, fermented milk, food products based on fermented milk, fermented cereals, flours, juices, sugar, cakes, ice creams, formulations for children, etc.

Medicament: throughout the description this term will refer to pharmaceutical compositions or formulations preferably designed to treat or prevent allergies, food allergies, intestinal inflammatory diseases, gastrointestinal infections and the translocation of pathogenic microorganisms or their toxins, alteration of the intestinal balance (dysbiosis), bacterial overgrowth, alteration of intestinal permeability, food intolerance, coeliac disease, malabsorption syndrome, etc.

Food composition: throughout the description this term will refer to foods (functional, conventional and novel), food supplements, formulae for nutritional purposes, and nutraceutical designed preferably to treat or prevent allergies, food allergies, intestinal inflammatory diseases, gastrointestinal infections and the translocation of pathogenic microorganisms or their toxins, alteration of the intestinal balance (dysbiosis), bacterial overgrowth, alteration of intestinal permeability, food intolerance, coeliac disease, malabsorption syndrome, etc.

Bioactive compound derived from a microorganism: any compound or molecule that forms part of the microorganism as a structural part, cellular component, subcellular fraction, metabolite or secreted molecule, obtainable by physical-chemical or biotechnological techniques, including among others centrifugation, filtration, lyophilisation, precipitation, sonication, mechanical and chemical cell disruption, compound extraction from cultures using enzymes and/or chemical agents, separation using chromatography techniques, cloning and over expression of the genes encoding the bioactive molecules that are capable of performing a function beneficial for health.

DETAILED DESCRIPTION OF THE INVENTION

Figure 1:
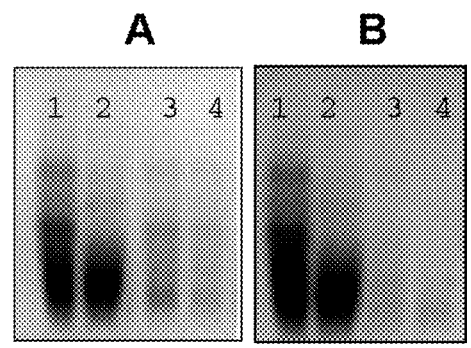
FIG. 1. SDS-PAGE analysis of the protein profiles of the different gliadin digestions. Panel A: 1) control of gliadins following digestion with pepsin (G-P); 2) control of gliadins following digestion with pepsin and trypsin (G-P-T); 3) G-P incubated with the strain of the invention; 4) G-P-T incubated with the strain of the invention (*Bifidobacterium* IATA-ES1). Panel B: 1) control G-P; 2) control G-P-T; 3) G-P incubated with the strain of the invention and *Lactococcus lactis* NCDO712; 4) G-P-T incubated with the strain of the invention and *Lactococcus lactis* NCDO712.

The present invention relates to a method for selecting microorganisms or strains of microorganisms capable of modulating the immune response in food allergies, which comprises: (a) isolating microorganisms from samples from healthy individuals, preferably breast-fed infants, and (b) selecting those microorganisms of the previous step capable of modulating the immune response and hydrolysing, inactivating or interfering with the mechanism of action of at least one agent that causes food allergies, preferably coeliac disease. Preferably, the microorganisms selected in step a) belong to potentially probiotic genera or species.

Another aspect of the invention relates to microorganisms capable of hydrolysing, inactivating or interfering in the action mechanism of at least one agent that causes food allergies and modulating the immune response. These microorganisms can be used preferably for the treatment or prevention of food allergies, intestinal inflammatory diseases, imbalances in the intestinal ecosystem (dysbiosis), bacterial overgrowth, malabsorption syndrome, gastrointestinal infections and translocation of pathogenic microorganisms or their toxins, and alterations of intestinal permeability.

The invention also provides microorganisms useful for producing formulations that reduce the risks and improve the state of health of individuals suffering or predisposed to suffer from disorders related to the ingestion of gluten by means of various mechanisms of action, characterised in that it is a non-genetically modified microorganism, isolated and selected from the intestinal microbiota of healthy individuals for its anti-inflammatory and regulatory properties.

Its multiple action mechanisms include for example, and without limiting the scope of the invention: (i) regulating the innate and adaptive immunological response caused by the toxic and immunogenic peptides of gluten; (ii) reducing the concentration of toxic epitopes in the intestinal lumen by means of the transport and hydrolysis of gluten peptides; (iii) strengthening the defensive barrier function against bacteria or other pro-inflammatory agents and with virulence factors isolated from the gastrointestinal tract of coeliac patients, and (iv) providing enzymatic activities, additional to peptidases, that favour digestion and supply of nutrients for alleviating the malabsorption syndromes typical of these patients. This microorganism could produce beneficial effects in addition to those mentioned, by way of illustration and without limiting the scope of the invention, reducing the oxidative stress associated to inflammation, regulating intestinal permeability, favouring the colonisation of beneficial Gram-positive bacteria with protective functions, regulating the function of antigen-presenting cells, inhibiting the interaction of toxic peptides with the host's immunocompetent and epithelial cells, interacting with metalloproteases, regulating the cell cycle and apoptosis, regulating cell growth and differentiation and regulating neuroendocrine functions. (De Stefano et al., 2007. Lycopene, quercetin and tyrosol prevent macrophage activation induced by gliadin and IFN-γ. Eur J. Pharmacol. 2; 566 (1-3):192-9; Silano et al., 2007. A decapeptide from durum wheat prevents celiac peripheral blood lymphocytes from activation by gliadin peptides. Pediatr Res. 61(1):67-71; Gross et al. 2007. Role of neuropeptides in inflammatory bowel disease. Inflamm Bowel Dis. 3(7):918-32).

The microorganisms of the invention belong, preferably, to the *Bifidobacterium* genus. The microorganisms of this genus offer advantages in the formulations of foods, novel foods, probiotics, synbiotics, supplements, nutraceuticals, and pharmaceutical formulations for the treatment or prevention of coeliac disease and related disorders. Bifidobacteria have a special ability to colonise the intestinal tract of newborns, contributing significantly to the development of their defences.

In a particular embodiment, the microorganisms of the invention belong preferably to the species *B. longum*. As an example, and without limiting the scope of the invention, the strain of the invention belonging to this species has been isolated from the faeces of healthy breast-fed infants and identified by sequencing of the 16S rRNA gene (Example 6) and the tuf gene. The isolated *Bifidobacterium* strain, Accession No. CECT 7347, was deposited with The Spanish Type Culture Collection (La Colección Española de Cultivos Tipo; CECT) (University of Valencia, Edificio de Investigacióon, Campus de Burjassot, 46100 Burjassot (Valencia) SPAIN) on Dec. 20, 2007. The sequenced fragment (SEQ ID NO: 1) (1437 bases) was amplified by PCR using primers 27f and 1401r and for the sequencing primers 530f and U-968f were also used in accordance with the procedures described by other authors (Satokari et al., 2001. Appl. Environ. Microbiol. 67, 504-513; Favier et al. 2002. Appl. Environ. Microbiol. 68, 219-226). By aligning the sequence obtained with those existing in the databases (GenBank), maximum similarity was detected with the sequences equivalent to 14 different strains of the species *B. longum* and among them *B. longum* BG3 (access number AY735403.1). Part of the tuf gene (498 pb) was amplified and sequenced using the primers described by Ventura et al. (Analysis, characterization, and loci of the tuf genes in *Lactobacillus* and *Bifidobacterium* species and their direct application for species identification. Appl Environ Microbiol. 2003; 69(11):6908-22). In this case maximum similarity was also detected with the species *B. longum* and specifically with the sequence corresponding to the strain *B. longum* ATCC 15707 (access number AY372042.1) following the same procedure.

This shows that *B. longum* presents ideal properties for regulating the immune system of the invention in a similar way as other appropriately selected strains of this genus and species could do so, providing the same beneficial effects in individuals with disorders related to the ingestion of gluten.

Another aspect of the invention relates to a bacterial strain that belongs to the species *B. longum* and which has been deposited in the Spanish Type Culture Collection (Colección Espanola de Cultivos Tipo—CECT), with headquarters in Burjassot (Valencia), on 20 Dec. 2007, corresponding to deposit number CECT 7347. This strain belongs to the species *B. longum* in accordance with the homology of the 16S rRNA gene sequence with others currently available in the databases (GenBank), as described in example 6; as well as with the homology of the tuf gene with that of other strains of this species. The latter constitutes an example of a strain of the *Bifidobacterium* genus possessing properties that allow its use in pharmaceutical formulations or medicaments, foods (new or functional) or nutritional or food supplements.

The microorganisms of the invention and, preferably, the strain of the invention, can be combined with other microorganisms and bioactive compounds to improve their protective and metabolic properties through synergic or complementary actions, such as the increase in total synthesis of regulatory cytokines and their types, the increase in the inhibitory capacity against pathogenic bacteria and of the intestinal barrier function, and the increase in the contribution of peptidases and other enzymes that favour digestion by increasing their total concentration or increasing their type and specificity.

Thus, another aspect of the invention comprises the combination of bifidobacteria with other microorganisms or bioactive compounds, in a complementary and/or synergic manner, favouring the immunoregulatory responses and the degradation of the toxic and immunogenic peptides of gluten. As an example of microorganisms, the strain *B. longum* ATCC 15707 can reinforce the immunomodulatory effect of the strain of the invention due to its high capacity to induce the synthesis of IL-10 as demonstrated in table 1 (Example 1); this action would also complement the induction of TGF-β produced only by the second strain (Table 1, Example 1). At the same time, the strain *Lactoccocus lactis* NCD0712 can complement and intensify the degradation of gluten peptides due to the bifidobacteria and thereby reduce the concentration of toxic epitopes of gluten and their intestinal and extra-intestinal damage due to the fact that it possesses, as well as intracellular peptidases, extracellular proteolytic activity. The intensification of the proteolytic activity is demonstrated in example 2 and in FIG. 1, where it is possible to appreciate an almost total disappearance of the protein bands following the incubation of the gliadin digested samples with cellular suspensions of the strain of the invention and *Lactoccocus lactis* NCD0712 (FIG. 1, panel B, lanes 3 and 4). This hydrolysis was higher than that obtained using only the strain of the invention (FIG. 1, panel A, lanes 3 and 4).

Another aspect of the invention relates to the use of the microorganisms of the invention, preferably the strain of the invention, as well as its no-viable equivalents inactivated by different procedures (freezing, heat, radiation, etc.) for immunomodulatory purposes.

The non-viable microorganisms of the invention inactivated by different procedures (freezing, heat, radiation, etc.) continue to be useful for therapeutic or preventive purposes and also form part of the present invention. The immunomodulatory effects of the bifidobacteria are produced, at least in part, by structural constituents (DNA, cell-wall components, etc.). This makes it possible for the bifidobacteria to maintain part of their immunomodulatory properties without necessarily maintaining viability (Lammers et al., 2003. Immunomodulatory effects of probiotic bacteria DNA: IL-1 and IL-10 response in human peripheral blood mononuclear cells. FEMS Immunol Med. Microbiol. 38: 165-72). Thus, example 3 and table 3, show that cellular suspensions of the strain of the invention, inactivated by cycles of freezing and thawing, can modulate the pro-inflammatory response triggered by gliadins when co-incubated with peripheral blood mononuclear cells, thereby reducing the synthesis of pro-inflammatory cytokines (for example IFN-γ) and increasing the synthesis of regulatory cytokines (for example IL-10).

Also, the derived bioactive compounds of the microorganism of the invention such as structural compounds, those resulting from metabolism, molecules secreted by any of the microorganisms or strain of the invention, obtained by well-known techniques, form part of the present invention and can also be used for modulating the immune responses. For example, physical-chemical and biotechnological techniques including among others centrifugation, filtration, lyophilisation, precipitation, sonication, mechanical and chemical cell disruption, extraction of compounds based on cultures with enzymes and/or chemical agents, separation by chromatography techniques, cloning of genes encoding said compounds and their overexpression.

Example 1 and table 1 show that the structural components that form part of the cell envelope of the bifidobacteria are responsible at least in part for the induction and production of regulatory cytokines (IL-10 and TGF-β). In example 3 and table 3 where gliadin digested samples have been co-incubated with unviable cell suspensions of the strain of the invention it is also shown that the structural components of these cells are capable of reducing the pro-inflammatory response brought about by gliadins and of increasing the synthesis of regulatory cytokines (IL-10). Likewise, structural components, metabolites and substances secreted by the strain of the invention exerted an inhibitory effect on the growth of potentially pathogenic bacteria isolated from coeliac disease patients, as demonstrated in example 4 and table 4. In the said example, the inhibitory effect of cell cultures of this strain has been evaluated using the double-layer technique wherein both the cells as well as the metabolites and secreted products are placed in contact with the pathogenic microorganism, in such a way that the inhibitory effects can be due to the synergistic action of all these components. The inhibitory effect of the metabolites and compounds secreted by the bifidobacteria into the culture medium has also been evaluated by using as an inhibitory agent the supernatants of cell-free cultures, previously lyophilised. Thus, it has been shown that the compounds released into the culture medium provide an inhibitory effect against the isolated potential pathogens of coeliac disease patients (Table 5).

In a particular embodiment of the present invention the microorganisms of the invention, the composition of the invention, the derived bioactive compounds of the invention, the supernatant of the invention, the extract of the invention, the pharmaceutical or nutritional composition of the invention, the strain of the invention, their cellular components or subcellular fractions, compounds resulting from their metabolism, secreted molecules and combinations thereof are characterised by being able to regulate or modulate the innate and adaptive immune response caused by the harmful peptides of gluten or other food allergies.

The strain of the invention has been selected for its immunomodulatory properties capable of regulating the Th1-type pro-inflammatory responses characteristic of coeliac disease and related diseases (Down's syndrome, diabetes mellitus type 1, dermatitis herpetiformis, myopathy, multiple sclerosis, arthritis, autism, schizophrenia, depression, lymphomas and ataxia), as well as Th2-type allergic reactions that can be caused as a result of the ingestion of wheat and other cereal proteins. The strains are characterised by their ability to induce a low production of the cytokine Th1 IFN-γ (for example <100 pm/ml) and of the pro-inflammatory cytokine IL-1 (for example <150 pm/ml) and by inducing a high production of the regulatory cytokines IL10 (for example >800 pm/ml) and TGF-β (for example >50 pmol/m) by peripheral blood mononuclear cells (PBMCs; Example 1, Table 1). The profile of cytokines induced by these bifidobacteria is not a characteristic common to all bifidobacteria and human intestinal lactic acid bacteria (Example 1, Table 1) and makes it especially ideal for modulating the anomalous immune response that wheat proteins bring about in predisposed individuals and in patients with an active coeliac disease. The detection of these immunomodulatory effects when using cellular suspensions of the strain selected as stimuli in these tests (Example 1 and table 1) indicates that the structural components that form part of the cell envelope of this bifidobacteria are responsible, at least in part, of inducing the regulatory cytokine production (IL-10 and TGF-β) which can reduce the toxic and immunogenic effects of gluten peptides. Also, in example 3 and table 3 it is shown that the use of unviable cellular suspensions of the strain of the invention (inactivated by cycles of freezing-thawing) co-incubated with gliadin digested samples are capable of reducing the synthesis of pro-inflammatory cytokines (for example INF-γ and IL-15) caused by the gliadins and increasing the synthesis of regulatory cytokines (for example INF IL-10). Therefore, it is demonstrated that structural components of the cells of the bifidobacteria can regulate the anomalous immunological responses caused by gluten, without it being strictly necessary to maintain the bacteria's viability.

The microorganisms of the invention, as well as the strain of the invention, derived bioactive compound of the invention, the cellular components thereof, compounds resulting from their metabolism, secreted molecules and combinations thereof are characterised by being able to strengthen the defensive barrier function against harmful bacterial, for example pro-inflammatory bacteria and bacteria with virulence factors, isolated from the gastrointestinal tract of coeliac disease patients.

The microorganisms of the invention are capable of inhibiting bacteria with pathogenic and toxic potential isolated from the intestine of coeliac disease patients (Example 4, Tables 4 and 5). These pathogens include, among others, strains of the species *Escherichia coli* which encode pathogenicity factors (for example fimbriae) and belong to virulent phylogenetic groups (for example, B2), strains of the genus *Bacteroides* and of other genera that produce metalloproteases which contribute to tissue injury, and haemolytic strains isolated from duodenal biopsies. In example 4 and table 4 the inhibitory effect of total cell cultures of this strain is demonstrated against the isolated pathogens of celiac disease patients, using the double-layer technique, in such a way that these effects can be due to structural components, metabolites and substances secreted by the strain of the invention. Table 5 also shows the inhibitory effect of the cell-free supernatants of the cultures of this strain that only contain the metabolites and compounds secreted by the bifidobacteria into this medium. In both cases the inhibition effects obtained using the selected strain are higher than those obtained using other strains assayed for comparative purposes. Thus, the microorganisms or the strain of the invention can contribute to restoring the intestinal ecosystem and reducing the antigenic load of microbial origin that would favour the inflammatory process and increase the permeability of the epithelium. Likewise, the selected strain is capable of inhibiting the synthesis of pro-inflammatory cytokines (for example IFN-$\gamma$ and TNF-$\alpha$) stimulated by the intestinal microbiota of coeliac disease patients in peripheral blood mononuclear cells. For example, concentrations of IFN-$\gamma$ of 90.8 and of TNF-$\alpha$ of 1966.3 pmol/ml produced by PBMCs under the stimulation with the microbiota of celiac disease patients can be reduced to values of 8.2 pmol/ml and 295.2, respectively, in the presence of the strain of the invention (Example 7). This strain is also capable of stimulating the synthesis of regulatory cytokines (IL-10), reduced at the same time by the intestinal microbiota of coeliac disease patients. Thus, for example values of IL-10 of 49.3 pmol/ml induced by the microbiota of coeliac disease patients can be increased up to values of 107.5 pmol/ml through stimulation of the *Bifidobacterium* strain IATA-H1. Through this immunomodulatory mechanism the selected strain can contribute to restoring intestinal balance and avoiding the over-stimulation of the immune system caused by the harmful microbiota that together with that caused by gluten can generate a vicious circle that perpetuates the inflammation.

Also, the microorganisms of the invention are characterised by their ability to transport the gluten peptides resulting from gastrointestinal digestion, thereby reducing the concentration of harmful epitopes.

Figure 2:
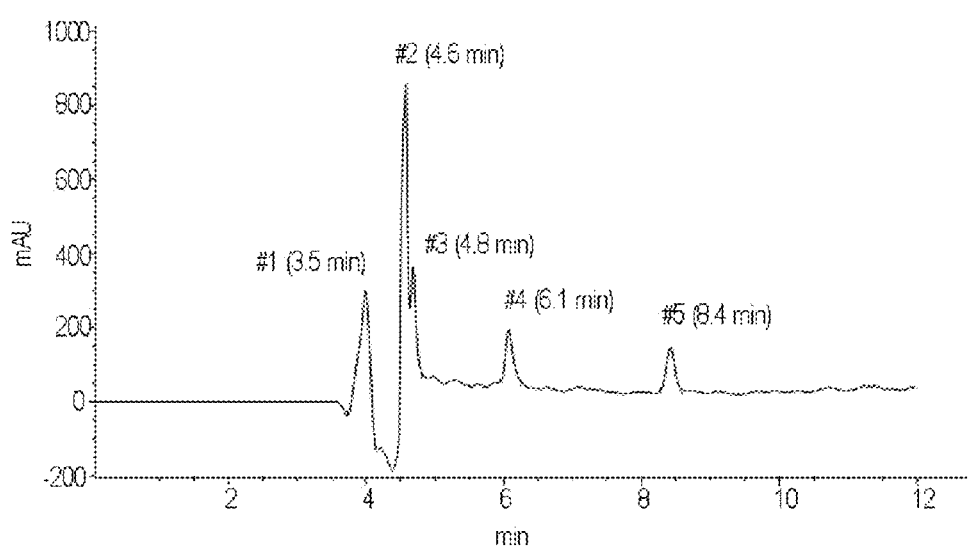
FIG. 2. Chromatogram obtained of the dialyzable fraction of the in vitro gliadin digestion. Peak 2 is the one preferably hydrolysed by the strain of the invention.

Specifically, the strain of the invention possesses the capacity to take up toxic peptides derived from the gastrointestinal digestion of gliadins, from products resulting from gastric digestion by means of the action of pepsin (P), as well as from intestinal digestion by means of the action of trypsin (T) and pancreatin (X) (Example 2, FIG. 1). The incubation of gliadins in the presence of viable bacteria of the selected strains reduces their concentration and the presence of toxic epitopes determined using the R5 antibody by ELISA sandwich and therefore their possible harmful effects in the intestine and at the extra-intestinal level. For example, the concentration of toxic epitopes of a gliadin sample digested with pepsin, trypsin and pancreatin (as indicated in Example 2) of 2349 ppm of gluten determined by ELISA sandwich was reduced to 169 ppm of gluten following incubation with cellular suspensions of the strain of the invention. Likewise, the incubation of the strain of the invention with gliadin digested in gastrointestinal conditions and dialysed, with a membrane of exclusion-size of less than 15 kDa, and subsequent analysis thereof by HPLC in inverse phase made evident the capacity of this bifidobacteria to reduce at least by 10% the concentration of fraction #2, which was the main fraction of digested gliadins and the one that contains immunogenic peptides identified by mass spectrometry, a property that the rest of the tested strains did not present (Example 8, FIG. 2). The biological effects on the intestinal epithelium of this property of the *B. longum* IATA-ES1 strain have been demonstrated following incubation of the different gliadin digested samples in Caco-2 cell cultures, as described in Example 8. This example demonstrates that the strain of the invention can thereby increase the viability of epithelial cells, unlike the rest of the tested strains (Example 8, FIG. 3). Additionally, the co-incubation of the strain of the invention with the gliadin digested sample decreased the latter's effect on the synthesis of pro-inflammatory cytokines such as TNF-alpha and the expression of the W13 factor responsible for the expression of pro-inflammatory genes (Example 8, FIG. 4).

The capacity of the microorganisms of the invention and preferably of the strain of the invention to capture the oligopeptides derived from gliadin digestion is reproduced in intestinal conditions and in the presence of bile salts. This capacity is potentiated by means of the co-incubation with *Lactococcus lactis* NCDO712 which, despite not managing to colonise the large intestine, can act as a co-adjuvant in the first stages of hydrolysis of ingested gluten by means of the action of its wall-anchored protease and other peptidases (Example 2, FIG. 1). The intensification of the proteolytic activity by means of the action of *Lactoccocus lactis* NCD0712 is demonstrated in FIG. 1 where an almost total disappearance of the protein bands can be appreciated following the incubation of the gliadin digested samples with cellular suspensions of the strain of the invention and *Lactoccocus lactis* NCD0712 (FIG. 1, panel B, lanes 3 and 4). This hydrolysis was greater than that obtained by using only the strain of the invention (FIG. 1, panel A, lanes 3 and 4). The activity of the bifidobacteria on the gluten can also be potentiated by means of its co-incubation with proteases and peptidases of *Lactococcus lactis* NCDO712 in the form of extracts.

The strain of the invention can modulate the abnormal immunological response caused by the interaction of the toxic peptides of gluten with the immunocompetent cells of the individual not only by means of metabolising the peptides which act as harmful antigens, but also by means of immunoregulatory mechanisms (Example 3, Table 3). The viable or inactivated bacterial suspensions of the selected strains co-incubated with PBMCs in the presence of gastrointestinal gliadin digested samples are capable of counteracting the pro-inflammatory effect of these proteins in different phases of digestion, by action of gastric pepsin (P) and of intestinal trypsin (T) and pancreatin (X). This strain is capable of inducing a reduction in the production of the pro-inflammatory cytokines IFN-$\gamma$, IL-1, IL-8 and IL15 responsible for the adaptive and innate immune response, as well as of increasing the synthesis of the regulatory cytokine IL-10 (Example 3, Table 3). These effects are due at least in part to the inhibition of the different subunits of the nuclear factor (NF) κB, p50, p65 (ReIA), c-Rel and Rel B determined by an ELISA assay (Trans AM NFκB, Active Motive, Belgium). The inhibition of this transcriptional factor entails the inhibition of the expression of a large number of pro-inflammatory genes representing a key control point of inflammatory processes and specifically of that occurring in coeliac disease (Jelinková et al., 2004. Gliadin stimulates human monocytes to production of IL-8 and TNF-alpha through a mechanism involving NF-κB. FEBS Lett. 571(1-3):81-5).

The microorganisms of the invention, derived bioactive compounds of the invention, their cellular components together with the compounds resulting from their metabolism, secreted molecules and combinations thereof are characterised by being able to hydrolyze gluten peptides by means of their peptidase activity, reducing the concentration of harmful epitopes. As an example, the strain of the invention has peptidases with broad specificity and with specificity for proline-containing substrates, which are very abundant in gliadins and limit their hydrolysis by conventional enzymes (Example 2, Table 2). Specifically, this strain is one of the ones with the highest iminopeptidase activity (>300 U/mg protein); likewise, it presents prolyl-endopeptidase activity (>8 U/mg protein), X-prolyl-dipeptidyl-peptidase (>15 U/mg protein), prolidase and prolinase activity (>15 U/mg protein). It also possesses tripeptidase activity (>130 U/mg protein against the substrate Gleu-Gly-Gly) and leucyl-aminopeptidase activity (>70 U/mg protein). The activity of this strain against proline-containing substrates, such as Pro-pNA, is higher than that detected in other lactic bacteria and especially the Pro-pNA/Leu-pNA activity ratio (Di Cagno et al. 2004. Sourdough bread made from wheat and nontoxic flours and started with selected lactobacilli is tolerated in celiac sprue patients. Appl Environ Microbiol. 70:1088-96; De Angelis et al. 2006. VSL#3 probiotic preparation has the capacity to hydrolyze gliadin polypeptides responsible for celiac sprue. Biochim Biophys Acta. 2006 1762(1):80-93), which favours the specific hydrolysis of gluten peptides with a high proline content.

Thus, the strain of the invention, derived bioactive compounds of the invention, cellular components, compounds resulting from its metabolism secreted molecules and combinations thereof, possess metabolic activity additional to that of peptidases (for example: phosphatase, esterase, lipase, galactosidase, glucosidase and N-acetyl-glucosaminidase) which help to digest the nutrients that are ingested with the diet, and improve the syndrome of malabsorption and malnourishment characteristic of coeliac disease patients.

Finally, another particular embodiment is the use of the microorganism of the present invention, derived bioactive compounds of the invention, cellular components, compounds resulting from its metabolism, secreted molecules and combinations thereof in combination with other microorganisms, in the production of formulations for reducing the risks and improving the state of health of patients with diseases related to the ingestion of gluten, or other food allergies.

The formulations prepared using the strain of the invention can be developed industrially giving rise to, among others and without limiting the scope of the invention, different forms of presentation to the consumer: foods (functional, conventional and novel), supplements, nutraceuticals, pharmaceutical compositions, probiotics and/or synbiotics, or new foods.

The strain of the invention possesses the ability to adhere to mucin (1-4%) and is resistant to the stomach's acid pH (2.0; 2.5 and 3.0) and at high concentrations of bile salts (0.5; 1.0; 2.0; and 3.0%) present in the small intestine, which constitute the main biological barriers that limit the survival of probiotics when they pass through the intestinal tract as well as during the processes of food fermentation and their storage period (Example 5, Table 6). For example, this strain maintains a viability and growth capacity of 56-86% following 90 min of incubation at pH 2.0-2.5. Therefore, this strain has higher probabilities of surviving and being functional than other isolated ones and some currently commercialised probiotics as can be seen from Table 6. This strain also resists gastrointestinal transit in vivo. Following its administration in the form of fermented milk during 4 weeks at doses of $10^7$-$10^8$ cfu/ml twice daily it is recovered in faeces and its concentration in respect of the initial concentration (without ingestion of probiotic products) increases by at least 1 logarithmic unit. The selected bifidobacteria grow and remain viable in various foods and drinks, constituting ideal carriers for their intake. For example, they are capable of fermenting and coagulating milk, they could be used for the preparation of fermented milks and other milk derivatives. They also resist technological treatments for the production and conservation of foods, supplements and pharmaceutical formulations, such as for example lyophilisation and refrigeration temperatures, guaranteeing their industrial exploitation.

A particular aspect of the present invention comprises the use of the microorganisms of the invention, the strain of the invention or derived bioactive compounds of the invention in the preparation of formulations in the form of foods.

In this way, the microorganisms of the invention can form part of a food formulated to provide, beyond its usual nutritional value, a beneficial effect on reducing the risks and improving the state of health of patients with diseases related to gluten ingestion.

Another particular aspect of the present invention comprises the use of the microorganisms, the strain of the invention, or the derived bioactive compounds of the invention in the production of preparations in the form of nutraceuticals, defined as natural bioactive substances presented in a non-food matrix, which in this case would produce beneficial effects in patients with diseases related to gluten ingestion, reducing their risks and improving their health status.

In the case of the use of the microorganisms, the strain of the invention or derived bioactive compounds of the invention to obtain a dietary or food supplement, it would include in its composition the microorganism or derived bioactive compounds thereof with a view to complementing the diet for health purposes and, in this specific case, for the purpose of producing beneficial effects in patients with diseases related to gluten ingestion, reducing their risks and improving their health.

Another particular aspect of the present invention comprises the use of the microorganisms of the invention, the strain of the invention or bioactive compounds of the invention in the production of pharmaceutical preparations. In this way, it would be used in the preparation of biologically active compositions, capable of being used as medicaments producing a beneficial effect on reducing the risks and improving the health status of patients with diseases related to gluten ingestion.

In another particular embodiment of the invention, the microorganisms of the invention, strain of the invention or bioactive compounds of the invention would be used in the production of probiotics and/or synbiotics (combinations of probiotics and prebiotics), where the microorganisms are incorporated, for example live or lyophilized, in suitable quantities and conditions that allow them to carry out their beneficial or therapeutic effect on individuals with foods allergies, preferably those related to the ingestion of gluten, thereby reducing their risks and improving their state of health.

A final particular objective of the present invention comprises the use of the microorganisms of the invention, the strain of the invention or bioactive compounds of the invention in the preparation of novel foods. Understanding new foods as meaning any food or ingredient that has not been commonly used in the past for human consumption in the European Union as of 15 May 1997, which would produce beneficial effects in patients suffering from diseases related to gluten ingestion, reducing their risks and improving their health status.

EXAMPLES OF EMBODIMENTS OF THE INVENTION

Example 1

Procedure for Selecting Strains of the *Bifidobacterium* Genus According to their Capacity to Modulate Cytokine Production in Peripheral Blood Mononuclear cells (PBMCs)

1. Preparation of the Cultures and Supernatants of the Bifidobacteria and other Intestinal Lactic Bacteria.

The strains were inoculated into 10 ml of MRS growth medium (Scharlau Chemie S. A., Barcelona, Spain) containing 0.05% of cysteine (MRS-C) at 1% with a culture of 24 h and were incubated during 22 h at 37° C. in anaerobiosis. (AnaeroGen; Oxoid, Basingstoke, UK). The cells were collected by centrifugation (6.000 g, 15 min), washed twice in PBS (10 mM sodium phosphate, 130 mM sodium chloride, pH 7.4), and were re-suspended in PBS containing 20% glycerol. Aliquots of these suspensions were frozen using liquid nitrogen and conserved at −80° C. The number of viable cells after the freezing-defrosting cycle was determined by counting on MRSC plates following incubation of 48 h. The viability was higher than 90% in all cases. Each aliquot was used for one single test. With a view to evaluating the effects of dead bacteria, some of the aliquots were cold-inactivated (3 freezing cycles at −20° C. and defrosting) and heat-inactivated (30 min. at 80° C.). The pH values of the supernatants obtained were adjusted to 7.2 using NaOH and were esterised by filtration (0.22-μm pore size, Millipore, Bedford, Mass.) to eliminate the possible presence of viable cells. Aliquots of the cell-free supernatants were conserved at −80° C. until further use.

2. PBMC Isolation and Stimulation

The PBMCs were isolated from the peripheral blood of 4 healthy volunteers (average age 30 years old, 24-40 range) in tubes with heparin. The PBMCs were isolated by centrifugation in Ficoll gradient (Amersham Biosciences, Piscataway, N.J.). The cells were washed with RPMI 1640 medium (Cambrex, N.Y., USA) and adjusted to a density of 1×10$^6$ cells/ml in RPMI 1640 medium containing additionally 10% bovine foetal serum (Gibco, Barcelona, Spain), 2 mM L-glutamine, 100 μg/ml streptomycin and 100 U/ml penicillin (Sigma). The PBMCs were incubated in flat-bottomed 24-well polystyrene plates (Corning, Madrid, Spain) in the presence or absence of stimulating agents at 37° C., at 5% of $CO_2$, during 24 h. Suspensions of live and dead bacteria were used as a stimulus at 1×10$^6$ CFU/ml, and supernatant volumes of 150 μl. As a positive control purified lipopolysaccharide (LPS) of *E. coli* O111:B4 was used (Sigma, St. Louis, Mo.) at a concentration of 1 μg/ml. As a negative control, the production of cytokines in non-stimulated PBMCs was tested. Each type of stimulus was tested in duplicate in each experiment. The supernatants of the cultures were collected by centrifugation, fractioned and stored in aliquots at −20° C. until cytokine detection.

3. Cytokine Determination

The concentrations of cytokines (IL-1, IFN-γ, IL-10, and TGF-β) of the supernatants were measured using ELISA Bioscience kits (BD Biosciences, San Diego, Calif.) following the instructions of the manufacturer.

TABLE 1

Immunomodulatory properties of the bifidobacteria and other intestinal lactic bacteria. Effect on the production of cytokines by PBMCs of viable bacteria.

| Stimulus | Cytokine production (pm/ml) | | | |
|---|---|---|---|---|
| | IL-1 | IFN-γ | IL-10 | TGF-β |
| RPMI | ND | 9.0 ± 1.0 | 58.0 ± 3.0 | ND |
| LPS | ND | 12.0 ± 0.5 | 399.0 ± 8.0 | ND |
| [1]ES1 | 103.0 ± 37.0 | 10.1 ± 1.0 | 2459.0 ± 28.0 | 236.0 ± 119.0 |
| [2]A2 | 255.0 ± 1.0 | 13.0 ± 2.0 | 699.0 ± 396.0 | ND |
| [3]ATCC15707 | — | 66.1 ± 23.9 | 4098.4 ± 1551.7 | — |
| [4]BIR-324 | ND | 11.0 ± 5.0 | 469.0 ± 15.0 | ND |
| [5]W11 | — | 160.4 ± 6.8 | 486.0 ± 236.4 | — |
| [6]BB536 | — | 143.7 ± 18.3 | 1390.0 ± 268.8 | — |
| [7]LM1V | 233.0 ± 99.0 | 27.0 ± 15.0 | 166.0 ± 53.5 | ND |

ND, not detected
—, not evaluated
[1]Strain of the invention (IATA-ES1),
[2]*Bifidobacterium* IATA-A2,
[3]*Bifidobacterium longum* ATCC15707,
[4]*Bifidobacterium* BIR-324,
[5]*Bifidobacterum longum* W11,
[6]*Bifidobacterum longum* BB536,
[7]*Lactobacillus reuteri* LM1V.

Example 2

Procedure for Selecting Bifidobacteria Capable of Hydrolysing and Transporting Gluten Peptides Thereby Reducing their Toxicity The capacity of the strains to hydrolyze the gluten-derived proteins and peptides was measured by quantifying the activity of broad-spectrum and specific intracellular peptidases for hydrolysing proline-containing peptide sequences, present in the peptides responsible for the immunological and toxic responses of gluten. The cells of bacterial cultures of 16-18 hours grown in MRSC were collected by centrifugation (9000×g for 10 minutes at 4° C.) washed twice in 50 mM Tris buffer at pH 7 and re-suspended in the same buffer concentrated 10 times in relation to the initial culture volume. The cells were mechanically disrupted using a Bead-Beater (Biospec Products, USA) adding 2 volumes of glass beads for each volume of cells and applying 2 pulses of 1.5 minutes. The supernatant obtained after centrifuging (8000 g, 10 min) to eliminate insoluble fragments and cells was used as an enzymatic extract for the activity tests. The tested substrates were as follows: Leu-paranitroanilide (-pNA) to detect broad specificity aminopeptidases, Leu-Leu-Gly to detect broad specificity aminopeptidases and tripeptidases, Suc-Ala-PropNA to detect prolyl-endopeptidases, Pro-AMC to detect iminopeptidases, Gly-Pro-AMC to detect X-prolyl-dipeptidil-peptidases; Val-Pro to detect prolidases, and Pro-Gly to detect prolinases. In the case of substrates derived from paranitroanilide, the reaction mixture consisted of 200 µl 50 mM phosphate buffer, at pH 7.2, containing 0.5 mM substrate and 50 µl enzymatic extract. The reaction mixture was incubated at 37° C. during a maximum of 30 min. The hydrolysis of the substrate and release of paranitroaniline was monitored at 419 nm in a spectrophotometer (550 Microplate Reader, Bio-Rad, Hercules, Calif., USA). The hydrolysis of the peptides was determined by means of the L-amino acid oxidase assay (Hejgaard, 1978, Rapad assay to detect peptidases in column effluent fractions using L-amino acid oxidase. Analytical Biochem 90: 835-839). 100 µl of the reaction buffer containing a concentration of 0.05 mM was incubated with 50 µl enzymatic extract during 20 min. Following this period 100 µl of the L-amino acid oxidase reagent was added and, after 5 minutes of incubation, the absorbance was measured at 530 nm. The protein concentration was measured using the Bradford method with the BioRad commercial kit (Hercules, Calif., USA). One unit of activity was defined as the amount of enzyme capable of hydrolysing 1 µmol of substrate at 37° C. during 1 minute. The activities were expressed in U/mg of protein.

samples were inactivated by incubation at 100° C. during 30 minutes. The bacterial suspensions were incubated in the presence of the three gliadin hydrolyzates (A, B and C) during 6 hours, at 37° C., in anaerobiosis. The changes in viability during the incubations were determined using the commercial system LIVE/DEAD BacLight Kit (Molecular Probes, Leiden, The Netherlands) for microscopy following the manufacturer's instructions. The counting of live bacteria (green) and dead (red) was carried out in an epifluorescence BX 51 Olympus microscope (Tokyo, Japan). In all cases minimum losses of viability were detected (0.0-11.5%) following incubation. After the incubation period it was centrifuged to eliminate insoluble cells and proteins and the supernatants were esterised by filtration (0.22-µm pore size, Millipore, Bedford, Mass.) to eliminate the possible presence of viable cells. The capacity of the strains to transport and use the different gliadin hydrolysates was determined by evaluating the disappearance of bands in conventional polyacrylamide gels at 15% and in Tris-Tricine gels (Ready gels 10-20% linear gradient, 4% stacking gel, Bio-Rad, Barcelona, Spain) for peptide separation. The proteins were visualised through staining with Coomassie Brilliant Blue R-250. The reduction in toxic epitopes resulting from the transport and digestion of gliadins through the action of the selected bacteria was evaluated using an ELISA sandwich R5 assay (Centro Nacional de Biotecnologia, Madrid).

TABLE 2

Peptidase activity of strains of bifidobacteria and lactobacilli of intestinal origin against synthetic substrates.

| | Specific activity (U/mg protein)* | | | | | | |
|---|---|---|---|---|---|---|---|
| Strains | Val-Pro | Pro-Gly | Leu-Gly-Gly | Pro-pNA | Leu-pNA | Suc-Ala-Pro-pNA | Gly-Pro-pNA |
| [1]ES1 | 18.1 ± 3.5 | 15.7 ± 3.8 | 132.3 ± 7.2 | 480.2 ± 91.7 | 80.0 ± 8.9 | 8.5 ± 1.9 | 17.1 ± 0.0 |
| [2]A2 | 27.1 ± 14.0 | 27.1 ± 07.5 | 326.1 ± 15.9 | 140.5 ± 6.4 | 176.5 ± 3.5 | 18.5 ± 4.8 | 60.43 ± 11.0 |
| [3]15707 | 27.4 ± 2.0 | 37.9 ± 0.8 | — | — | 5.1 ± 0.5 | 0.02 ± 0.6 | 0.2 ± 0.5 |
| [4]LmV1 | 9.34 ± 0.7 | 10.3 ± 0.6 | 54.6 ± 2.7 | 7.8 ± 3.7 | 61.8 ± 3.4 | 8.0 ± 3.5 | 15.2 ± 3.2 |

*Media ± SD.
—, not evaluated
[1]Strain of the invention (IATA-ES1),
[2]*Bifidobacterium* IATA-A2,
[3]*Bifidobacterum longum* ATCC15707,
[4]*Lactobacillus reuteri* LM1V.

The capacity of the strains to transport and hydrolyze the peptides derived from the digestion of gliadins was determined by electrophoresis. In this case, the cellular suspensions were adjusted to an optical density of 4 at 655 nm, equivalent to $10^9$ cfu/ml, and were incubated with three different gliadin hydrolysates at a final concentration of 300-600 µg/ml in PBS to which 0.2% of glucose was added. The gliadin hydrolysate (Sigma, St. Louis, Mo.) were obtained by simulating the process of gastrointestinal digestion in the following manner: A). 100 g of gliadins were digested in one liter of HCL 0.2 N (pH: 1.8) with 2 g of purified pepsin at 37° during 2 h (this hydrolyate will be referred to as G-P). B) The resulting digestion was digested with trypsin by adding 2 g of trypsin after adjusting the pH to 8 using 2N NaOH (this hydrolysate will be referred to as G-P+T). C) The double digested sample was then treated with 2 g of pancreatin and stirred during 2 hours at pH 8 (this hydrolyzate will be referred to as G-P+T+X). Following each stage of digestion it was centrifuged at 10.000 g during 10 min, and the supernatant was stored for further tests at −20° C. The digested Example 3

Regulation of the Immunological Response Caused by Gliadins in Immunocompetent Cells by Means of Their Co-Incubation with Strains of the *Bifidobacterium* Genus Selected for their Immunomodulatory Properties Suspensions of the selected strain ($10^6$-$10^9$ CFU/ml), as well as others included for comparative purposes, were incubated with the different gliadin hydrolyzates (P, P+T and P+T+P), obtained as described in example 3, and PBMCs at a concentration of $10^6$ cfc/ml during 24 h. As control stimuli the different gliadin hydrolyzates were used without bacteria and LPS of *E. coli* O111:B4. Basal cytokine production was also detected without adding any stimulus. The procedure for isolating PBMCs, stimulating and detecting cytokines was described in example 1.

TABLE 3

Production of cytokines by PBMCs stimulated simultaneously by gliadins digested in gastrointestinal conditions and in the presence of unviable cultures of bifidobacteria and other lactic bacteria of intestinal origin.

| | Cytokine production (pm/ml) | | | | |
|---|---|---|---|---|---|
| Stimulus | IL-1 | IL-8 | IFN-γ | IL-10 | IL-15 |
| RPMI | ND | 173 ± 17 | 9 ± 1 | 58 ± 3 | ND |
| LPS | ND | 2295 ± 83 | 12 ± 0.5 | 399 ± 8 | 175 ± 17 |
| G–P | 61 ± 2 | 4570 ± 484 | 42 ± 7 | 299 ± 149 | 34 ± 1 |
| G–P+T | 169 ± 22 | 5375 ± 13 | 37 ± 3 | 136 ± 16 | 149 ± 83 |
| G–P+T+X | 75 ± 1 | 5264 ± 122 | 36 ± 9 | 272 ± 18 | 25 ± 7 |
| [1]ES1/G–P | 123 ± 8 | 4921 ± 129 | 11 ± 1 | 1192 ± 752 | 10 ± 7 |
| ES1/G–P+T | 48 ± 4 | 4928 ± 288 | 8.2 ± 5 | 935 ± 426 | 27 ± 10 |
| ES1/GP+T+X | ND | 5151 ± 146 | 2 ± 0.5 | 1054 ± 477 | ND |
| [2]A2/G–P | 109 ± 215 | 4480 ± 23 | 6.9 ± 2 | 395 ± 216 | 29 ± 8 |
| A2/G–P+T | 129 ± 4 | 2848 ± 45 | 43 ± 22 | 1002 ± 615 | 46 ± 13 |
| A2/G–P+T+X | 129 ± 1 | 5099 ± 30 | 29 ± 4 | 1314 ± 724 | 134 ± 57 |
| [3]LM1V/G–P | ND | 5152 ± 119 | 62 ± 31 | 721 ± 16 | 33 ± 4 |
| LM1V/G–P+T | ND | 5015 ± 75 | 11 ± 5 | 458 ± 218 | 26 ± 4 |
| LM1V/G–P+T+X | ND | 5189 ± 98 | 82 ± 35 | 457 ± 257 | 6 ± 1 |

ND, not detected
[1]Strain of the invention (IATA-ES1)
[2]*Bifidobacterium* IATA-A2
[3]*Lactobacillus reuteri* LM1V Example 4

Capacity of the Selected Bifidobacteria to Inhibit the Growth of Isolates of the Intestinal Mirobiota of Coeliac Disease Patients with Pathogenic Potential The antimicrobial activity of the strains of the *Bifidobacterium* genus previously selected according to their immunomodulatory properties following the procedure described in Example 1, was determined by means of two methods: (i) the double-layer technique and (ii) the agar diffusion technique.

The antibacterial activity of each strain was evaluated globally by means of the double-layer technique using as indicator microorganisms, bacteria isolated from the intestinal microbiota of coeliac disease patients and with pathogenic potential. The bifidobacteria were grown in MRS-C plates in lines of about 2 cm and were incubated in optimum conditions during 16 h and their subsequent development was inhibited using chloroform. The indicator microorganism was inoculated at a concentration of $10^4$-$10^5$ CFU/ml into 10 ml of suitable semi-solid agar, poured over the layer of agar of the protective microorganism and incubated at 37° C. in anaerobiosis. Following 24 h the inhibition haloes around the culture lines of the bifidobacteria were measured.

In order to evaluate the antibacterial activity due to the secretion of protein-nature compounds the technique of diffusion in agar was used. 10 ml of MRS-C growth medium was inoculated at 1% with a culture of 24 h of each bifidobacteria and incubated during 16 h at 37° C. The supernatants were obtained by centrifugation (12.000 g, 15 min, 4° C.) and concentrated by lyophilization. The lyophylised samples were re-suspended in 1 ml of 50 mM phosphate buffer at pH 6.5, neutralised with NaOH until reaching a pH of 6.5 to eliminate the effects of the organic acids generated by fermentation, and sterilised by filtration. These samples constituted crude extracts in which the possible activity of antibacterial proteins produced by the bifidobacteria was determined. The indicator microorganism was inoculated at a concentration of $10^4$-$10^5$ cells/ml into 10 ml of suitable semi-solid agar and poured over a solid layer of agar of the same medium. After solidifying, wells of 5 mm were perforated, to which 40 μl of the cell-free and neutralised extract of each bifidobacteria was added. It was allowed to diffuse for 4 h at 4° C. and was subsequently incubated in optimum conditions for the indicator or pathogenic microorganism. Following incubation the inhibition haloes around the well were measured.

TABLE 4

Inhibition of potentially pathogenic bacteria isolated from coeliac patients by cultures of the bifidobacteria.

| | Inhibition (cm) by the *Bifidobacterium* strains | |
|---|---|---|
| Strains | IATA-A2 | IATA-ES1 |
| *Bacteroides* CAQ4 | 0.4 | 1.4 |
| *Bacteroides vulgatus* | 0.5 | 1.3 |
| *Clostridium difficile* | 0.9 | 1.6 |
| *E. coli* CBE9 | 1.1 | 1.9 |
| BC-BP1 | 0.5 | 1.2 |
| BC-BO1 | 0.7 | 1.0 |
| BC-BU1 | 2.3 | 2.0 |
| BC-BU3 | 1.0 | 1.3 |

TABLE 5

Inhibition of potentially pathogenic bacteria isolated from coeliac patients by supernatants of the bifidobacteria cultures.

| | Inhibition (cm) by *Bifidobacterium* spp. | |
|---|---|---|
| Indicator strain | IATA-A2 | IATA-ES1 |
| Bac CAQ4 | 0.40 | 0.45 |
| Ent CBE9 | 0.95 | 1.15 |

Example 5

Evaluation of the Resistance of the Bifidobacteria to Conditions of Gastrointestinal Stress The resistance of the isolated bifidobacteria to the acid conditions of the gastric juices, which constitute the first biological barrier limiting the viability of probiotics following ingestion, was confirmed for each one of the recovered strains. To do this, cell suspensions of each strain were prepared ($10^8$ cells/ml) in PBS, containing 3 g/l of pepsin (Sigma, St. Louis, Mo.) and adjusted to pH 2 with HCl and were incubated at 37° C. during a total of 120 min. At different times (0, 90 and 120 min), including the average time of gastric emptying (90 min), aliquots were taken to determine the viability through counts in agar MRS-C plates. Subsequently, the tolerance of acid-pH-resistant strains to other stress conditions such as bile, NaCl and high temperatures, was studied. To know the tolerance of the strains studied to bile tolerance, their capacity to grow was evaluated in MRS-C, to which various concentrations (0.5-1.5%) of Ox-gall (Sigma, St. Louis, Mo.) were added. Aliquots of 200 μl of each medium, inoculated at 1% with cultures of 24 h, were loaded on multi-well plates and incubated at 37° C. The growth was monitored using absorbance measurements at 655 nm in a 550 Microplate Reader spectrophotometer (Bio-Rad, Hercules, Calif.).

ingested foods containing bifidobacteria for at least one month prior to the analysis and who had not been given any treatment with antibiotics. The samples were kept at 4° C. and were analysed without more than two hours having passed since their collection. Two grams of each one were diluted in 10 mM phosphate buffer containing a 130 mM concentration of NaCl (PBS) and were homogenised in a Lab-Blender 400 stomacher (Seward Medical, London, UK) during 3 min, and then diluted in peptone water. Aliquots of 0.1 ml of various decimal dilutions were inoculated in MRS agar (of Man Rogosa and Sharpe; Scharlau, Barcelona) containing 0.05% of cysteine (Sigma, St. Louis, Mo.; MRS-C), and 80 μg/ml of mupirocin. Following 48-hour incubation at 37° C. in conditions of anaerobiosis (AnaeroGen, Oxoid, UK) isolated colonies were selected and their identity was confirmed by means of a study of their morphology under Gram staining. The identity of the isolates was confirmed by genus-specific PCR, according to the methodology described by Kaufman et al. (1997, Identification and quantification of *Bifidobacterium* species isolated from food with genus-specific 16S rRNA-

TABLE 6

Effect of the gastric conditions on the growth capacity and viability of the *Bifidobacterium* strains

| | Viability * | | | Growth capacity † pH | | | | | | |
|---|---|---|---|---|---|---|---|---|---|---|
| | (%) | | | | 3 | | 2.5 | | 2 | |
| | pH | | | | Log | | Log | | Log | |
| Strains | 3 | 2.5 | 2 | Control | cfu/ml | (%) | cfu/ml | (%) | cfu/ml | (%) |
| IATA-ES1 | 99.4 ± 4.2 | 86.2 ± 13.0 | 57.9 ± 2.3 | 9.3 ± 0.0 | 9.3 ± 0.0 | 99.7 | 8.1 ± 0.0 | 86.7 | 5.2 ± 0.0 | 56.1 |
| BIR 324 | 89.4 ± 2.3 | 73.1 ± 1.0 | 61.6 ± 1.7 | 9.1 ± 0.0 | 8.8 ± 0.0 | 96.9 | 8.8 ± 0.2 | 96.8 | 5.79 ± 0.1 | 63.6 |
| Bion 3 | 98.4 ± 1.9 | 78.4 ± 1.7 | 11.6 ± 3.7 | 9.0 ± 0.0 | 7.3 ± 0.0 | 81.2 | 4.8 ± 0.1 | 52.8 | — | — |
| NCIMB 8809 | 1.8 ± 0.5 | — | — | 8.1 ± 0.0 | — | — | — | — | — | — |

* Viability expressed as the percentage of viability detected using the LIVE/DEAD BacLight Kit system (Molecular Probes) in cellular suspensions in PBS at pH 7.2, which was considered to be 100%.
† Growth capacity expressed in Log cfu/ml determined by counting in MRSC agar plates and expressed as a percentage of the recount of the cell suspension in PBS, which was considered to be 100%.
*, † Mean standard deviations of the results obtained in three independent tests
nd, not determined
—, not detected

TABLE 7

Tolerance of the *Bifidobacterium* strains to the presence of bile salts
Relative growth capacity *(% □)
Concentration of oxgall (%)

| Strains | Control | 0.5 | 1.0 | 2.0 | 3.0 |
|---|---|---|---|---|---|
| IATA-ES1 | 100 | 88.22 ± 0.70 | 82.65 ± 1.60 | 69.95 ± 0.33 | 67.28 ± 1.31 |
| A2 | 100 | 73.03 ± 0.98 | 64.12 ± 1.79 | 60.96 ± 0.59 | 38.21 ± 1.44 |
| BIR 324 | 100 | 62.68 ± 3.55 | 43.99 ± 1.64 | 38.29 ± 0.32 | 37.06 ± 0.48 |
| NCIMB 8809 | 100 | 45.07 ± 8.20 | 23.88 ± 7.56 | 3.94 ± 1.05 | 0.70 ± 1.00 |
| Bion 3 | 100 | 30.17 ± 3.2 | 23.30 ± 0.0 | — | — |

* Data expressed as a percentage of the speed of growth ($h^{-1}$) obtained in the absence of bile, which was considered to be 100%. Mean standard deviations of the results obtained in three independent experiments.

Example 6

Isolation and Identification of the Selected Bifidobacteria

The strains of the genus *Bifidobacterium* were isolated from the faeces of healthy breast-fed infants who had not targeted probes by colony hybridization and PCR. Appl. Environ. Microbiol. 63:1268-1273), using the primers (LM26 and LM3) which amplify a 1.35 kb fragment of the ribosomal 16S RNA gene. Also, the 16S rRNA gene was sequenced from total DNA. The sequenced fragment was amplified using primers 27f and 1401r and was purified using the GFX™PCR commercial system (Amershan, Bioscience, UK). For the sequencing, the primers 530f and U-968f were also used following the procedures described by other authors (Jonson, 1994. Similarity analysis of rRNAs. In Methods for General and Molecular Bacteriology; Gerhard, P.; Murray, R. G. E.; Wood, W. A.; Krieg, N. R., Eds. American Society for Microbiology, Washington, D.C. Pp 683-700; Satokari et al., 2001. Bifidobacterial Diversity in Human Feces Detected by Genus-Specific PCR and Denaturating Gradient Gel Electrophoresis. Appl. Environ. Microbiol. 67, 504-513; Favier et al. 2002. Molecular Monitoring of Succession of Bacterial Communities in Human Neonates. Appl. Environ. Microbiol. 68, 219-22). The sequencing was carried out using an automatic DNA sequencer ABI 3700 (Applied Biosystem, Foster City, Calif.). The search for the closest related sequences was carried out in the GenBank database using the BLAST algorithm (Altschul et al., 1990. Basic local alignment search tool. J. Mol. Biol. 215, 403-410).

Example 7

Evaluation of the Capacity of Strains of the *Bifidobacterium* Genus to Regulate the Pro-Inflammatory Responses Caused by the Altered Intestinal Microbiota of Coeliac Individuals with Active Disease and after Treatment with a Gluten-Free Diet.

1. Preparation of the Intestinal Bifidobacteria Cultures and Faecal Samples for Evaluation.

The strains of the *Bifidobacterium* genus were inoculated into 10 ml of MRS growth medium (Scharlau Chemie S. A., Barcelona, Spain) containing about 0.05% of cysteine (MRS-C) at 1% with a culture of 24 h and were incubated during 22 h at 37° C. in anaerobiosis. (AnaeroGen; Oxoid, Basingstoke, UK). The cells were collected by centrifugation (6.000 g, 15 min), washed twice in PBS (10 mM sodium phosphate, 130 mM sodium chloride, pH 7.4), and re-suspended in PBS containing 20% glycerol. Aliquots of these suspensions were frozen using liquid nitrogen and conserved at −80° C. The number of viable cells following the freezing-thawing cycle was determined by recounting on MRSC plates following incubation for 48 h. The viability was higher than 90% in all cases. Each aliquot was used for one single test.

Faeces from coeliac patients with the active disease (at the moment of diagnosis) and treated with a gluten-free diet for at least 2 years were diluted 1/10 in phosphate buffer, homogenised in a stomacher for 3-5 minutes and frozen at −20° C. for use as a stimulus in peripheral blood mononuclear cells. Faeces samples from healthy individuals were also taken as controls.

2. Isolation and Stimulation of PBMCs

The PBMCs of the peripheral blood of 4 healthy volunteers (average age 30 years old, range 24-40) were isolated in tubes with heparin. The isolation of PBMCs was carried out by centrifugation in Ficoll gradient (Amersham Biosciences, Piscataway, N.J.). The cells were washed in RPMI 1640 medium (Cambrex, N.Y., USA) and adjusted to a density of $1 \times 10^6$ cells/ml in RPMI 1640 medium containing also 10% bovine foetal serum (Gibco, Barcelona, Spain), 2 mM L-glutamine, 100 μg/ml streptomycin and 100 U/ml penicillin (Sigma). The PBMCs were incubated in flat-bottomed 24-well polystyrene plates (Corning, Madrid, Spain) in the presence or absence of stimulating agents at 37° C., at 5% of $CO_2$, during 24 h. As a stimulus extracts of the faeces of healthy individuals, active and non-active coeliac disease patients were used, in the presence or absence of 30 μl of live bacterial cell suspensions of $1 \times 10^6$ CFU/ml. As a positive control purified lipopolysaccharide (LPS) of *E. coli* O111:B4 was used (Sigma, St. Louis, Mo.) at a concentration of 1 μg/ml. As a negative control cytokine production in non-stimulated PBMCs was tested. Each type of stimulus was tested in duplicate in each experiment. The supernatants of the cultures were collected by centrifugation, fractioned and stored in aliquots at −20° C. until cytokine detection.

3. Determination of Cytokines and Cellular Activation Markers

The concentration of cytokines (IFN-γ, IL-10, and TGF-β) of the supernatants was measured using ELISA kits of Bioscience (BD Biosciences, San Diego, Calif.) following the instructions of the manufacturer. The markers of the different lymphocyte populations and of activation were detected using antibodies anti CD4, CD8 and CD86 labelled with FITC (eBioscience, San Diego, Calif.) and flow cytometry (Flow cytometer EPICS® XL-MCL; Beckman Coulter, Fla.). The implication of the signal transduction pathway mediated by the nuclear factor (NF) KB in the immune response was determined by adding an inhibitor thereof (lactacystine).

Results

The faeces of coeliac disease patients, which presented alterations in the composition of the microbiota, induced a production of pro-inflammatory cytokines (TNF-α and IFN-γ) higher than that of healthy individuals and a production of the anti-inflammatory cytokine IL-10 lower than that of healthy individuals in PBMCs. They also increased the synthesis of the surface molecule CD86 essential for the activation of T-cells more than the control faeces. The co-incubation with bifidobacteria regulates the profile of pro-inflammatory cytokines induced by the faecal microbiota of celiac disease patients, reducing the synthesis of TNF-α and IFN-γ and increasing that of IL-10. The inhibition of the synthesis of cytokines in the presence of lactacystine suggests that the NF κB is involved in the immunomodulatory effects exerted by the *bifidobacteria*.

Example 8

Characterisation of the Fractions of Gliadins Generated in the In Vitro Digestion Process and Characterisation of the Reduction of Peptides Derived from The Gastrointestinal Digestion of Gliadins by *Bifidobacteria* and their Biological Effects 1. Gastrointestinal Gliadin Digestion A commercial preparation of gliadins was used (Sigma, G3375) which contains four of the isoforms, α-/β-, γ-, and ω-gliadins, of these proteins whose complete amino acid sequence is available.

The solution of different aliquots (150 mg) of the commercial extract of gliadins was carried out in an isotonic saline solution (140 mM NaCl, 5 mM KCl) at pH 3, heating the mixture to 55° C. during 30 minutes in a bath with stirring. The samples were subjected to a process of simulated gastrointestinal digestion using pepsin (Sigma, P7000) (800-2500 UI/mg protein) and porcine pancreatin (P1750) (activity, 4xUSP), and bile extract (B3883).

The gastric digestion (pepsin in 0.1M HCl/pH 3/1 h, stirring) was carried out in centrifugation tubes (50 ml). Subsequently, the intestinal stage (pancreatin-bile in 0.1M NaHCO3/pH 6.9-7/2 h, stirring) was carried out in the upper compartment (giver) (1.5 ml) of a bicameral system prepared with a dialysis membrane (Spectra/Por 2.1, Spectrum Medical, Gardena, Calif.) with a pore size of 15 KDa. In the bottom compartment (receiver) a saline solution was placed (1 ml). Once the digestion process was completed the total protein content was quantified in the supernatant (4000 rpm/5 min/4° C.) of the gastrointestinal digested sample and in the dialysated sample using a commercial kit (Sigma, TP0200) based on the Lowry method.

2. Chromatographic Analysis of the Gliadin Fractions Following the In Vitro Digestion Process.

To analyse the gliadins a chromatography method was adapted in reverse phase. The separation was carried out in a BioBasic C18 column (5 μm 4.6×250 mm) using Hewlett Packard 1050 HPLC equipment. The mobile phases used consist of (A) Acetonitrile (ACN, HPLC quality) aqueous at 15% (v/v) with Trifluoroacetic acid (TFA) 0.1% (v/v), and (B) ACN aqueous at 80% (v/v) with TFA 0.1% (v/v). The elution gradient used was as follows; 0-5 min., linear gradient up to 5% of the solvent B; 5-12 min., linear gradient up to 20% of the solvent B. The column was washed with 100% of the solvent B during 5 minutes, and was rebalanced using the initial conditions during 3 minutes. The samples were filtered through a nylon membrane (13 mm 0.22 μm Millex GN, Millipore). Three independent aliquots of each treatment were analysed (100 µl). The absorption in the ultraviolet region was monitored at 210 nm.

3. Identification of the Peptide Sequences of Gliadins Using Reverse Phase Chromatography Coupled to Electrospray-MsMs (RP-HPLC-ESI-MS/MS).

The chromatographic separation was carried out in a BioBasic C18 column (5 µm 4.6×250 mm) using an Agilent HPLC system equipment coupled to a mass spectrometer with a quadrupole ion trap (Esquire-LC-Ms(n), Bruker Daltonics, Billerica, Mass.). The chromatographic elution gradient employed was the one described in the previous section. In the analysis nitrogen was used as nebuliser and drying gas, and helium as the gas for molecular collision at an approximate pressure of 5×10-3 bar. The capillary voltage of collision was maintained at 4 kV. The mass spectra were monitored in the mass/load range of 500-5000. The method shows the mean mass analysis of (Ms) 15 spectra, and the sequential mass analysis Ms(n) of 5 spectra. The limit of ion current for carrying out the mass sequential analysis was established as 5000, and the precursor ions were isolated in a m/z range of 4.0 fragmented with a voltage ramp of 0.39 to 2.6 V. The m/z spectral data was processed and transformed using the analysis software provided by the manufacturer (Data Analysis version 3, Bruker Daltonics). The peptide sequences of the spectra Ms(n) were established using analysis software (BioTools version 2.1 (Bruker Daltonics).

4. Effects of the Co-Incubation of the Gastrointestinal Digested Gliadins with *Bifidobacteria*.

Figure 3:
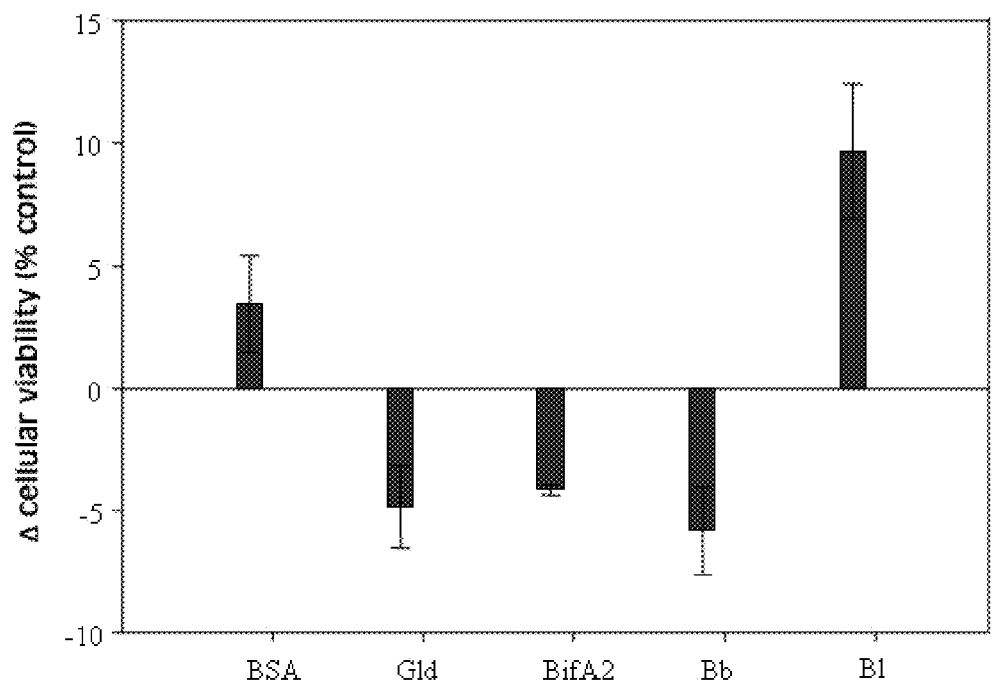
FIG. 3. Alteration of cell viability (measured as endolysosomal activity) caused by the soluble and digested fraction of gliadins (Gld), in the presence or absence of bifidobacteria in vitro. Bovine albumin–BSA—(negative control); BifA2 (*B. animalis*); Bb (*B. bifidum*) and BL (Strain of the invention—*Bifidobacterium longum* IATA-ES1—). The results are expressed in mean values and standard deviations are determined in quadruplicate.
Figure 4:
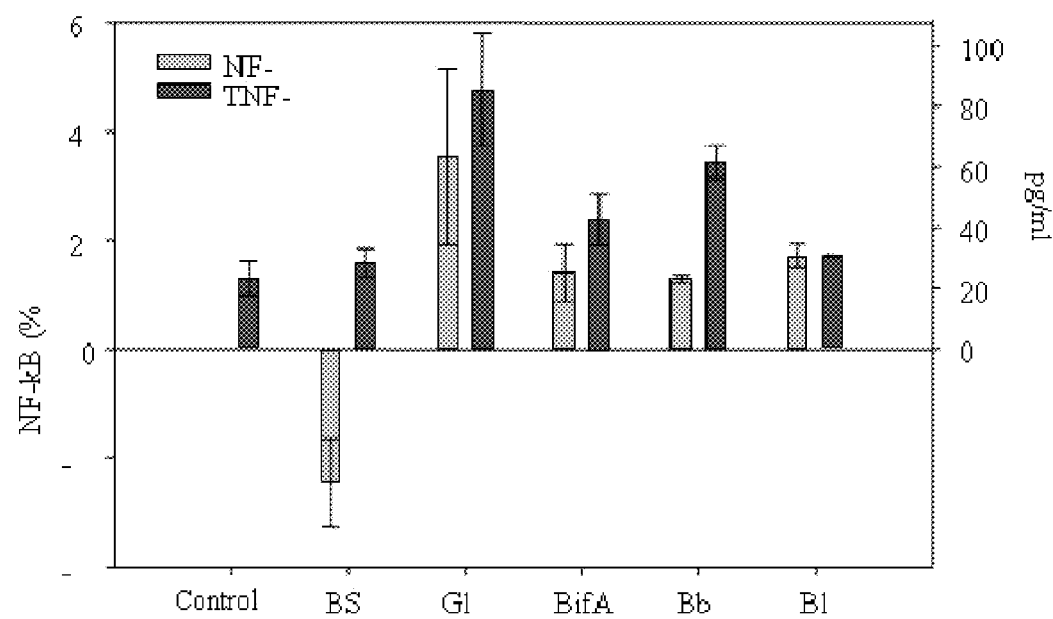
FIG. 4. Production of pro-inflammatory cytokines (TNF-α) and expression of the nuclear factor KB (NF-κB) in Caco-2 cell cultures exposed to the soluble and digested fraction of gliadins (Gld), in the presence or absence of bifidobacteria in vitro. Bovine albumin—BSA—(negative control); BifA2 (*B. animalis*); Bb (*B. bifidum*) and BL (Strain of the invention—*B. longum* IATA-ES1—). The results are expressed in mean values and standard deviations are determined in quadruplicate.

The gastrointestinal digested gliadin samples obtained in section 1 was co-incubated in the presence and absence of intestinal bifidobacteria, such as the strain of the invention, situated in the apical part (giver) of a culture in transwell of Caco-2 cells, used as intestinal epithelium model. For the purpose of estimating the reduction of the toxic effect of the gliadins in the presence of the strain of the invention (IATA-ES1), the synthesis of the pro-inflammatory cytokine TNF-α and NFκB was measured using ELISA methods in the Caco-2 cell culture of the bottom chamber (receiver) in the presence and absence of the bifidobacteria (FIGS. 3 and 4).

Results

RP-HPLC analysis of the protein fraction of less than 15 KDa derived from the dialysis of the gastrointestinal gliadin digested samples. The chromatographic separation (FIG. 2) reveals the presence of five peptide fractions the main one being fraction #2. Studies of the dialysability of the gliadin-derived peptides in the presence of different bacterial strains (i.e., strain of the invention (IATA-ES1) and *Bifidobacterium* A2, isolated in our laboratory demonstrated the proteolytic capacity of these bacteria on gliadins and specifically on fraction #2. The strain that caused the most important reduction of fraction #2 was the strain of the invention (IATA-ES1), which reduced more than 10% of the fraction in the study conditions.

Example 9

Evaluation of the Capacity of Strains of the *Bifidobacterium* Genus to Regulate the Gliadin-Induced Maturation and Pro-Inflammatory Phenotype in Dendritic Cells Involved in Antigen Presentation.

1. Preparation of the Cultures of Intestinal Bifidobacteria and Faeces Samples for Evaluation.

The strains of the *Bifidobacterium* genus were inoculated into 10 ml of MRS growth medium (Scharlau Chemie S. A., Barcelona, Spain) containing 0.05% of cysteine (MRS-C) at 1% with a culture of 24 h and were incubated during 22 h at 37° C. in anaerobiosis (AnaeroGen; Oxoid, Basingstoke, UK). The cells were collected by centrifugation (6.000 g, 15 min), washed twice in PBS (10 mM sodium phosphate, 130 mM sodium chloride, pH 7.4), and were re-suspended in PBS containing 20% glycerol. Aliquots of these suspensions were frozen using liquid nitrogen and conserved at −80° C. The number of viable cells following the freezing-thawing cycle was determined by counting in MRSC agar plates following incubation for 48 h. The viability was higher than 90% in all cases. Each aliquot was used for one single test. Before using the cells as stimulus they were washed by centrifugation and were re-suspended in PBS.

2. Isolation and Stimulation of Dendritic Cells (DC) Obtained from Peripheral Blood.

The PBMCs were isolated from the peripheral blood of 4 healthy volunteers (average age 30 years old, range 24-40) in tubes with heparin. The PBMCs were isolated by centrifugation in Ficoll gradient (Amersham Biosciences, Piscataway, N.J.). The cells were washed with RPMI 1640 medium (Cambrex, N.Y., USA) and were adjusted to a density of $1 \times 10^6$ cells/ml in RPMI 1640 medium containing also 10% bovine foetal serum (Gibco, Barcelona, Spain), 2 mM L-glutamine, 100 µg/ml streptomycin and 100 U/ml penicillin (Sigma). The PBMCs were incubated in flat-bottomed 24-well polystyrene plates (Corning, Madrid, Spain) in the presence or absence of stimulating agents at 37° C., at 5% of $CO_2$, during 24 h. As a stimulus gliadin was used (0.1 mg/ml) and IFN-γ (150 UI) in the presence and absence of bifidobacteria and other intestinal bacteria. As a positive control purified lipopolysaccharide (LPS) of *E. coli O* 111:B4 was used (Sigma, St. Louis, Mo.) at a concentration of 1 µg/ml. As a negative control the cytokine production in non-stimulated PBMCs was tested. Each type of stimulus was tested in duplicate in each experiment. The supernatants of the cultures were collected by centrifugation, fractioned and stored in aliquots at −20° C. until cytokine detection.

3. Determination of Cytokines and Cellular Activation Markers

The concentrations of cytokines (IFN-γ, IL-10, and TGF-β) of the supernatants were measured using ELISA kits of Bioscience (BD Biosciences, San Diego, Calif.) following the instructions of the manufacturer. The markers of activation molecules were detected using antibodies against HLA-DR, CD86, CD40 and CD83 labelled with FITC (eBioscience, San Diego, Calif.) and were quantified by flow cytometry (Flow cytometer EPICS® XL-MCL; Beckman Coulter, Fla.).

Results

The strain of the invention (IATA-ES1) reduced by at least 10% the production of IFN-γ, the main inflammatory cytokine that is produced in response to gliadins in coeliac disease patients, provoked by the stimulation of the dendritic cells with gliadins and other potentially pro-inflammatory intestinal bacteria (e.g. *bacteroides* and enterobacteria isolated from coeliac disease patients). This strain also produced an increase in the synthesis of the anti-inflammatory cytokine IL-10 by dendritic cells of at least 200% in comparison to the effect produced by the stimulation with gliadins. The strain of the invention (IATA-ES1) reduced the expression of HLA-DR and CD86 molecules, induced following the incubation of the dendritic cells in the presence of gliadin and IFN-γ, by between 15 and 20%.

The invention claimed is:

1. An isolated *Bifidobacterium longum* strain deposited at the Colección Española de Cultivos Tipo (CECT) under the accession number CECT 7347 having a proteolytic capacity on gliadins producing at least peptidases with improved specific activity over the substrate Pro-pNA.

2. The strain as claimed in claim 1, in the form of viable cells.

3. The strain as claimed in claim 1, in the form of non-viable cells.

4. An isolated combination of microorganisms, which comprises the strain as claimed in claim 1 and at least one other microorganism.

5. The isolated combination of microorganisms as claimed in claim 4 wherein the at least one other microorganism is *B. longum* ATCC 15707 and/or *L. lactis* NCD0712.

6. A method of treating a disorder relating to gluten ingestion comprising:
administering to a subject in need thereof a therapeutically effective amount of a *Bifidobacterium longum* strain deposited at the Colección Española de Cultivos Tipo (CECT) under the accession number CECT 7347, wherein the administration treats a disorder relating to gluten ingestion.

7. The method of claim 6, wherein administering regulates innate and adaptive immune responses caused by the harmful peptides of gluten.

8. The method of claim 6, wherein administering strengthens the defensive barrier function against harmful bacteria isolated from the gastro-intestinal tract of coeliac disease patients.

9. The method of claim 6, wherein administering favours digestion and supply of nutrients.

10. The method of claim 6, wherein administering favours the hydrolysis of gluten peptides.

11. The method of claim 6, wherein the subject suffers from coeliac disease.

12. A composition in the form of a nutritional composition selected from a food or a supplement, a nutraceutical, a pharmaceutical composition, a probiotic, a synbiotic, or a combination thereof, the composition comprising an isolated *Bifidobacterium longum* strain deposited at the Colección Española de Cultivos Tipo (CECT) under the accession number CECT 7347 having a proteolytic capacity on gliadins producing at least peptidases with improved specific activity over the substrate Pro-pNA.

13. The composition of claim 12, further comprising a carrier.

14. The composition of claim 12 further comprising a carrier wherein the carrier is milk, yoghurt, cheese, fermented milk, cereals, fermented cereals, juices, ice-creams, or formulations for children.

15. The composition of claim 12, wherein the *B. longum* strain is present in an amount from about $10^6$ cfu to about $10^9$ cfu per gram or milliliter of the composition.

16. The composition of claim 12, wherein the composition is in the form of a tablet, capsule, microcapsule, powder, solution, or paste.

17. A pharmaceutical composition comprising a pharmacologically acceptable excipient and an isolated *Bifidobacterium longum* strain deposited at the Colección Española de Cultivos Tipo (CECT) under the accession number CECT 7347 having a proteolytic capacity on gliadins producing at least peptidases with improved specific activity over the substrate Pro-pNA.

* * * * *

SEQUENCE LISTING

<160> NUMBER OF SEQ ID NOS: 1

<210> SEQ ID NO 1
<211> LENGTH: 1437
<212> TYPE: DNA
<213> ORGANISM: Bifidobacterium sp.

<400> SEQUENCE: 1

```
gcgccagggc ggcgtgctta cacatgcaag tcgaacggga tccatcaggt tttgcttggt      60
ggtgagagtg ggcaataggt gagtaatgcg tgaccgacct gccccataca ccggattagc     120
tcctggaaac gggtggtaat gccggatgct ccagttgatc gcatggtctt ctgggaaagc     180
tttcgcggta tgggatgggg tcgcgtccta tcagcttgac ggcggggtaa cggcccaccg     240
tggcttcgac gggtagccgg cctgagaggg cgaccggcca cattgggact gagatacggc     300
ccagactcct acgggaggca gcagtgggga atattgcaca atgggcgcaa gcctgatgca     360
gcgacgccgc gtgagggatg gaggccttcg ggttgtaaac ctcttttatc ggggagcaag     420
cgagagtgag tttacccgtt gaataagcac cggctaacta cgtgccagca gccgcggtaa     480
tacgtagggt gcaagcgtta tccggaatta ttgggcgtaa agggctcgta ggcggttcgt     540
cgcgtccggt gtgaaagaca taaagttaac ggtggatccg cgccgggtac gggcgggcct     600
taatgaggta ggggagactg gaattcccgg tgtaacggtg aatgtgtag atatcgggaa      660
gaacaccaat ggctcaaggc aggtctctgg gccgttactg acgctgagga gcgaaagcgt     720
ggggagcgaa caggattaga taccctggta gtccacgccg taaacggtgg atgctggatg     780
tggggcccgt tccacgggtt ccgtgtcgga tctaacgcgt taagcatccc gcctggggag     840
tacggccgcg gggctaaaac tcaaagaaat tgacgggggc ccgcagaggc ggcggattat     900
gcggattaat tcgctgcaac gcgaagaatc ttacctgggc ttgatttgtt cccgactgtc     960
gtacagatac ggcttcctct tcggggacgg gttcacaggt ggtgcatggt cgtcgtccag    1020
tctcgtgtcg tgagatgttg ggttaagtcc cgcaacgagc gcaaccctcg ccccgtgttg    1080
ccagcggatt atgccgggaa ctcacgggggg accgccgggg ttaactcgga ggaaggtggg    1140
gatgacgtca gatcatcatg ccccttacgt ccagggcttc acgcatgcta caatggccgg    1200
tacaacggga tgcgacgcgg cgacgcggag cggatccctg aaaaccggtc tcagttcgga    1260
tcgcagtctg caactcgact gcgtgaaggc ggagtcgcta gtaatcgcga atcagcaacg    1320
tcgcggtgaa tgcgttcccg ggtcttgtaa cacaccgaat gacgactgtt gttaggtcac    1380
ccgcggctgg cagtgaccgt atccatcgat gtccggtgat aactaaggag agagggt      1437
```